US011871926B2

(12) United States Patent
Fox

(10) Patent No.: US 11,871,926 B2
(45) Date of Patent: Jan. 16, 2024

(54) SURGICAL STAPLER

(71) Applicant: William Fox, New Richmond, OH (US)

(72) Inventor: William Fox, New Richmond, OH (US)

(73) Assignee: Jenei LLC

( * ) Notice: Subject to any disclaimer, the term of this patent is extended or adjusted under 35 U.S.C. 154(b) by 0 days.

(21) Appl. No.: 17/521,048

(22) Filed: Nov. 8, 2021

(65) Prior Publication Data
US 2022/0395272 A1 Dec. 15, 2022

Related U.S. Application Data

(63) Continuation-in-part of application No. 17/345,350, filed on Jun. 11, 2021.

(51) Int. Cl.
*A61B 17/072* (2006.01)
*A61B 17/068* (2006.01)

(52) U.S. Cl.
CPC ........ *A61B 17/072* (2013.01); *A61B 17/0686* (2013.01); *A61B 2017/07228* (2013.01); *A61B 2017/07235* (2013.01); *A61B 2017/07242* (2013.01); *A61B 2017/07264* (2013.01); *A61B 2017/07271* (2013.01); *A61B 2017/07285* (2013.01)

(58) Field of Classification Search
CPC ...... A61B 17/1155; A61B 2017/07257; A61B 2017/07271; A61B 2017/07285
USPC .............. 227/179.1–182.1; 606/75, 219, 220
See application file for complete search history.

(56) References Cited

U.S. PATENT DOCUMENTS

| | | | | |
|---|---|---|---|---|
| 5,205,459 | A * | 4/1993 | Brinkerhoff | A61B 17/115 227/19 |
| 8,113,406 | B2 * | 2/2012 | Holsten | A61B 17/1114 227/176.1 |
| 10,413,297 | B2 * | 9/2019 | Harris | A61B 17/068 |
| 2005/0075657 | A1 * | 4/2005 | Bombard | A61B 17/1152 606/153 |
| 2008/0210738 | A1 * | 9/2008 | Shelton | A61B 17/0643 227/176.1 |
| 2011/0290851 | A1 * | 12/2011 | Shelton, IV | A61B 17/07207 227/176.1 |
| 2012/0012638 | A1 * | 1/2012 | Huang | A61B 17/1114 227/176.1 |
| 2012/0168487 | A1 * | 7/2012 | Holsten | A61B 17/32 227/176.1 |
| 2013/0026209 | A1 * | 1/2013 | Mozdzierz | A61B 17/1155 227/176.1 |

(Continued)

*Primary Examiner* — Dariush Seif
(74) *Attorney, Agent, or Firm* — Jenei LLC

(57) ABSTRACT

A surgical stapler is disclosed herein. The surgical stapler comprises a body having a distal end and a proximal end, and the body defines an interior space. A first knob and a second knob are configured adjacent the proximal end of the body. An anvil and trocar assembly is configured adjacent the distal end of the surgical stapler, wherein the anvil and trocar assembly is coupled to the first knob, and the first knob is configured to facilitate the extension and retraction of the anvil and trocar assembly at the distal end of the body. A staple and knife assembly is configured adjacent the anvil and trocar assembly within the body, wherein the staple and knife assembly is coupled to the second knob, and wherein the second knob is configured to facilitate firing of staples and actuation of a knife of the staple and knife assembly sequentially.

17 Claims, 32 Drawing Sheets

(56) References Cited

U.S. PATENT DOCUMENTS

| | | | |
|---|---|---|---|
| 2013/0181035 A1* | 7/2013 | Milliman | A61B 17/1155 227/180.1 |
| 2014/0166727 A1* | 6/2014 | Swayze | A61B 17/1155 227/175.1 |
| 2015/0014393 A1* | 1/2015 | Milliman | A61B 17/1155 227/176.1 |
| 2016/0030046 A1* | 2/2016 | Williams | A61B 17/072 227/181.1 |
| 2016/0106418 A1* | 4/2016 | Shi | A61B 17/1155 227/175.2 |
| 2016/0249945 A1* | 9/2016 | Shelton, IV | A61B 17/068 606/171 |
| 2016/0367239 A1* | 12/2016 | Mumaw | A61B 17/0467 |
| 2017/0056008 A1* | 3/2017 | Shelton, IV | A61B 17/068 |
| 2019/0008518 A1* | 1/2019 | Sgroi, Jr. | A61B 17/1155 |
| 2019/0200996 A1* | 7/2019 | Shelton, IV | G16H 40/63 |
| 2020/0046356 A1* | 2/2020 | Baxter, III | A61L 31/022 |
| 2020/0054338 A1* | 2/2020 | Shen | A61B 17/1155 |
| 2020/0078016 A1* | 3/2020 | Swayze | A61B 17/072 |
| 2021/0038223 A1* | 2/2021 | Schings | A61B 17/07207 |
| 2022/0395272 A1* | 12/2022 | Fox | A61B 17/0686 |

\* cited by examiner

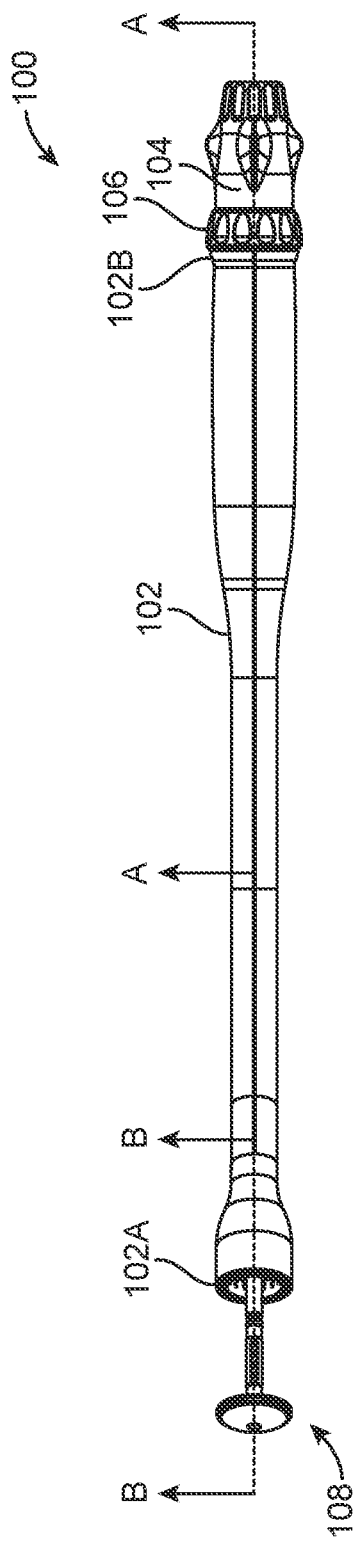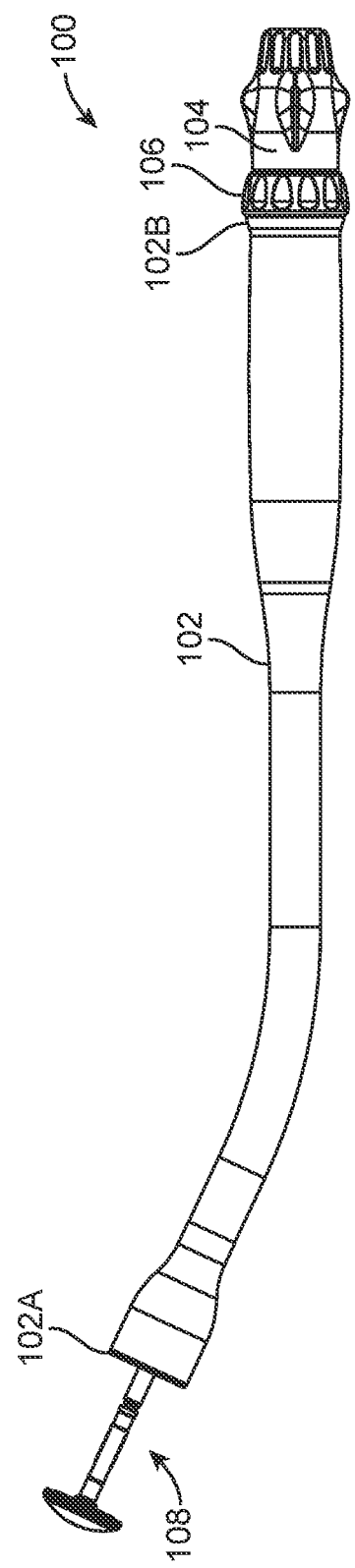
FIG. 1C
FIG. 1D

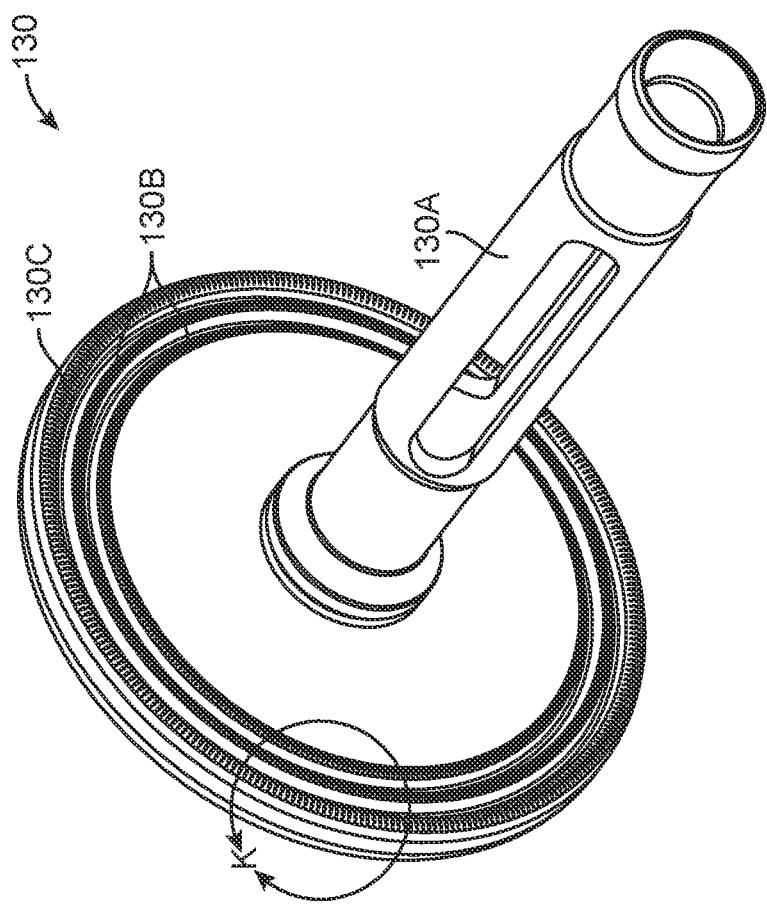

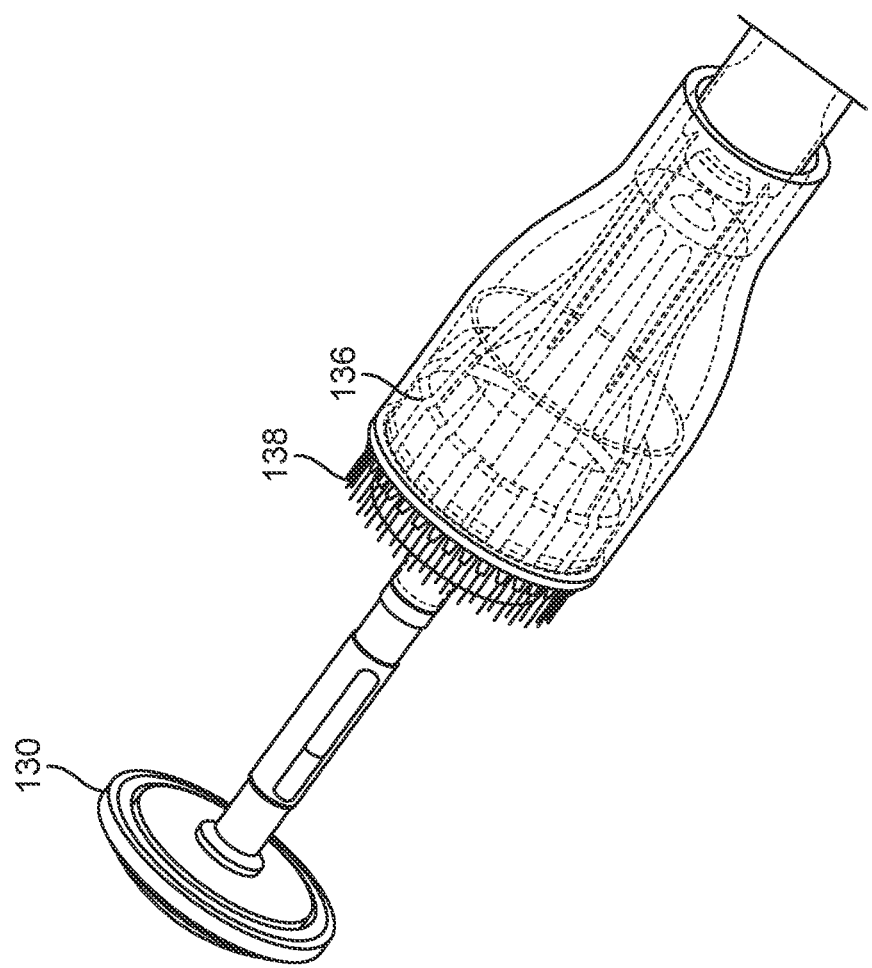

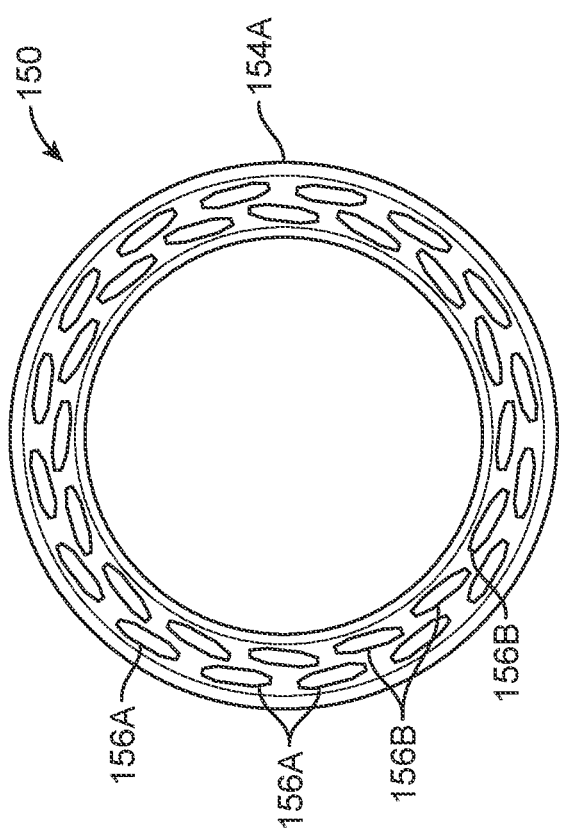

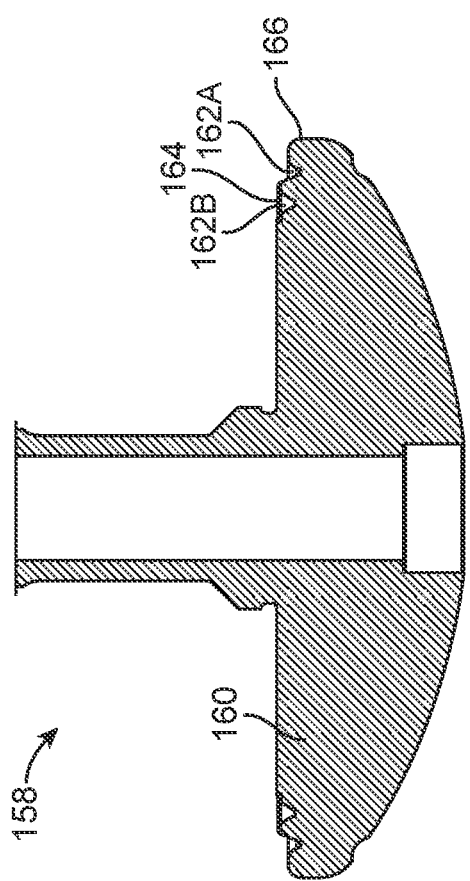
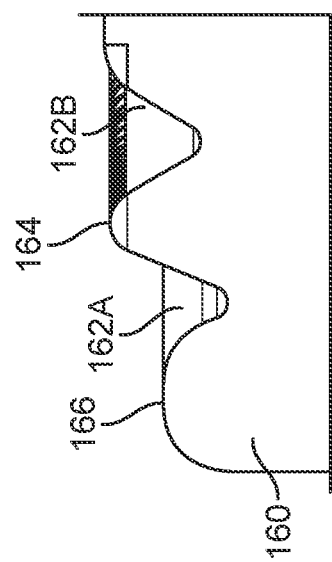
FIG. 11A
FIG. 11B

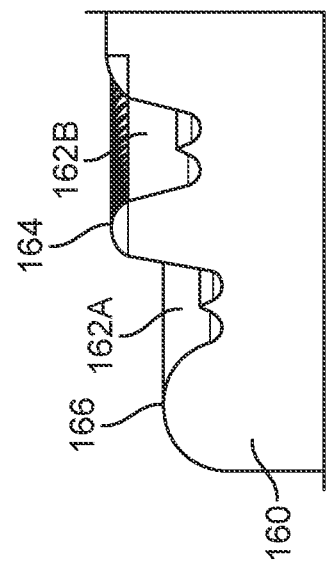
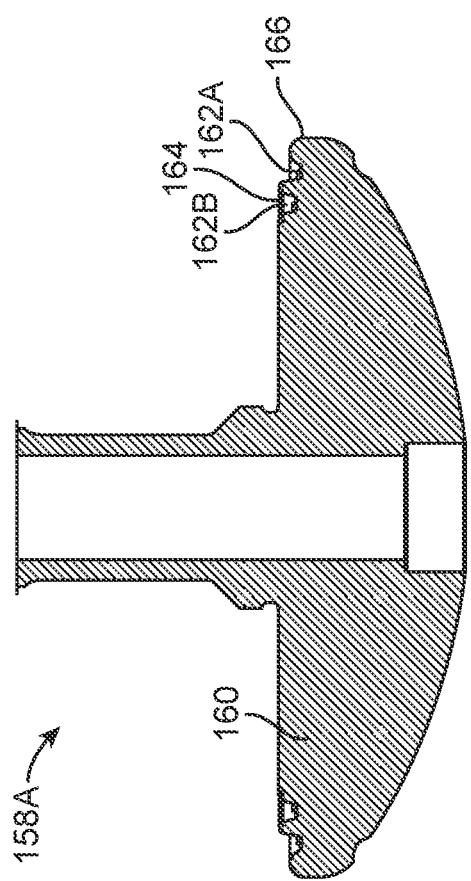
FIG. 12B
FIG. 12A

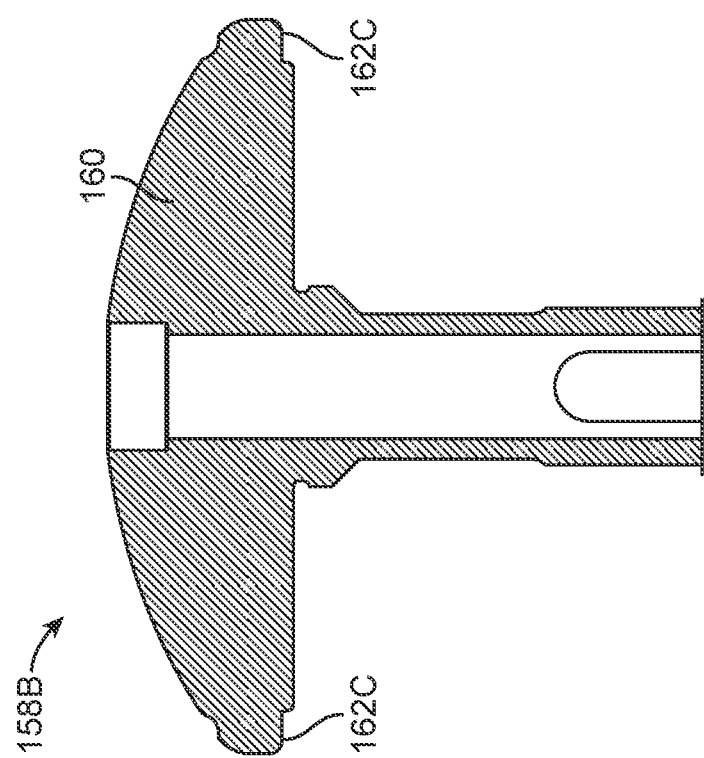

SURGICAL STAPLER

CROSS-REFERENCE TO RELATED APPLICATIONS

The present application for patent is a continuation-in-part (CIP) of patent application Ser. No. 17/345,350 entitled "SURGICAL STAPLER" filed Jun. 11, 2021, pending, the contents of which are hereby incorporated by reference in their entirety for any purpose.

TECHNICAL FIELD

The present invention generally relates to all surgical staplers and cutters currently used globally, whether open, laparoscopic, or endoscopic, and more particularly, to a new surgical stapler having a simpler design, enabling higher staple density patterns to prevent leakage and bleeding, and a simpler method of reliably and more consistently forming staples using components that are easier and less expensive to manufacture.

BACKGROUND

In a many surgical procedures (colorectal, general, bariatric, thoracic, etc.), portions of a patient's digestive tract, vascular structures, mesentery, and lung tissues are divided and/or removed to eliminate undesirable or diseased tissue, or a variety of other clinical reasons. Typically, the remaining viable tissues, and also the specimen to be removed, must be sealed to prevent contents leakage, contamination, and/or bleeding of the structures into the operative site. Further, according to the needs of a specific procedure, the divided structures typically comprising hollow organs, bladders, pouches, and tubular structures (vessels, bronchus, and alimentary structures) must be reconnected to restore functional viability, absent the segment of diseased or redundant tissue. This reconnection is frequently accomplished via the use of surgical stapling devices comprising many device configurations, shapes, and sizes adapted to fit the anatomical structures being fastened and modified. The device end effectors and shapes range in format (e.g., curved, circular, or linear), with some having integral cutters to divide the tissues after stapling, and some without said cutters. The stapling aspect and components of these devices generally comprise malleable metal staples that are typically formed by dispensing the staples from a cartridge or housing, piercing the staple tips though tissue layer(s) to be joined, with each staple tip contacting a sloped receiving surface, ultimately forming B-shaped final forms when wire legs of the staples are formed by discrete receiving pockets in an anvil, and which receiving pockets comprise multiple pairs of generally symmetrical indentations, one indentation per staple leg, much like a conventional desktop stapler used in offices and homes around the world.

Examples of surgical instrument configurations most often used to provide division of tissues with sealed cut edges include linear, curved, and circular staplers, which accomplish their clinical missions by transforming staples from an open U-shape to a B-shape to clutch and retain tissue. Surgical staplers operate by clamping and squeezing layers of tissue, cutting through the clamped layers, and driving staples through the clamped tissue layers and forming the staples to a closed final position to substantially seal the layers of tissue together near the severed ends or edges of tissue layers, thereby joining the two severed ends together, with minimal bleeding and not leakage of hollow organ contents. Circular, curved, and linear staplers may be configured to seal and sever the tissue substantially simultaneously or sequentially. For instance, a circular stapler may sever the excess tissue that is interior to a newly placed annular array of staples of an anastomosis, to ultimately provide a joint that results in a substantially smooth transition between the newly joined anatomical lumen sections, through which bowel contents can freely pass.

Circular staplers and other stapling and cutting devices of various shapes may be used in open, laparoscopic, or endoscopic procedures. In many instances, the distal portion of the circular stapler is inserted through a patient's naturally occurring orifice.

The present invention described herein solves multiple problems with existing devices now commercially offered, while simultaneously reducing the component count and their complexities, and thereby the corresponding costs, manufacturing steps, and simplifying the supply chains required to manufacture the finished devices and their components. The present circular stapler embodiment of the primary invention offers a novel and unique approach to staple formation, and additionally multiple features that allow clinicians to easily and reliably fire the staplers to complete surgical procedures in less time, simplify and reduce the number of steps necessary to actuate stapling devices, and quickly effect the trouble-free and smooth release of the surgical stapling and cutting devices from tissue, while providing a broader tissue thickness range of staple application, and elimination of adverse clinical events due to bleeding and leakage. Although the primary embodiment described herein comprises a circular stapling format, the revised anvil configuration is applicable and useful in all surgical stapling devices, regardless of anvil shape, device configuration, or clinical tissue fastening application, and regardless of whether they include or do not include knives cutters.

Conventional commercial devices utilize two discrete and often symmetrically ramped pockets to form each staple; with one leg-forming pocket for each staple leg, and with each pocket comprising an inclined striking surface to bias and effect staple leg formation in a certain direction. Discrete pockets require tight tolerances, which mandate challenging and expensive manufacturing processes and tooling, and critically located features that are expensive and difficult to consistently manufacture. And if pocket dimensions and locations vary only slightly, such deviations from near perfection can degrade the proper formation and final shape of surgical staples, negatively impacting the finished staple form, and consequentially the clinical performance of the staples to achieve hemostasis and leak prevention, both of which are crucial for safe use of the devices, and prevention of injury or death resulting from inadequately formed staples.

The use of surgical staplers has become one of the most preferred methods for joining of tissues in most surgical procedures, due to relative consistency and reliability compared to sutures and the technique sensitivity of suture application. Circular staplers have been developed in the art for usage in surgical procedures involving the lower colon, upper bowel, stomach, and other areas of the alimentary tract. More specifically, in some surgical procedures, sections of the lower colon are required to be joined together subsequent to the excision of a diseased section of the lower colon. Further, linear staplers and cutters are used in the transection of various tissues during many procedures, and which can also utilize attributes of the current invention for the purpose of versatility and manufacturing cost-reduction.

A typical circular surgical stapler includes a body having an actuating mechanism configured proximally, and a stapling mechanism configured distally. The stapling mechanism generally includes a fixed or sometimes replaceable staple cartridge that includes a multiplicity of staples configured in a circular array. A circular knife is concentrically mounted in an inner space defined by the staple cartridge for axial extension and retraction therein. Typically, a trocar extends axially upwards from the body for facilitating the axial displacement of the circular knife and the staple cartridge to interact with a staple anvil removably coupled thereto. A typical staple anvil is configured to bend the ends of the staples as the staples are inserted and fed into the staple anvil. The displacement of the staple cartridge with respect to the anvil is regulated via the actuating mechanism configured proximally on the body for controlling or maneuvering the trocar. The tissues that are to be joined are clamped between the staple cartridge and the staple anvil is simultaneously stapled and cut when the actuating mechanism is activated by the surgeon.

A disadvantageous aspect of the conventional circular staplers is the configuration of the staple anvil. A typical staple anvil includes pockets configured in accordance with the arrangement of the staple cartridge within the stapler. Due to such a design, each circular stapler has a corresponding staple anvil design depending on the number of staples in the staple cartridge. This is not desired, as the pockets limit the staple pattern and number of staples to what is determined by each specific cartridge and staple count, and the pockets must be nearly perfectly radially aligned between the cartridge and anvil to ensure proper symmetrical staple forms, making manufacturing especially of anvil and related components difficult and expensive.

Another disadvantageous aspect of the conventional staplers is that the actuation of the staples and the knife is designed to be simultaneous, causing in some cases the staples not being fully formed before the knife begins cutting tissue. This is not desirable, as it is quite possible that the knife cuts the tissue prior to completely attaching the segments of bowel or other tissue, thereby causing the tissue between the anvil and the staple cartridge to be incompletely sealed and joined, even though the tissue is already cut, thereby causing leakage, bleeding, and the need for reoperation, or in a worst-case scenario, patient death or serious injury.

Yet another disadvantageous aspect of the conventional circular staplers is the unnecessarily complicated design and the sheer number of components most circular staplers include. A high number of components directly contributes to higher manufacturing costs of the stapler and increases the probability and opportunity of malfunction due to manufacturing errors.

Yet another disadvantageous aspect of the conventional circular staplers is the difficulty of firing the device due to the high force to squeeze the firing lever to form the staples and cut the knife backing washer and tissue. The present invention solves this problem by eliminating the firing lever which requires a large hand grip and two-fisted grip to squeeze, and instead using a combination of improvements including the use of a high-mechanical-advantage firing system comprising a drive screw, low coefficient of friction components, and pre-bent staples with smaller wire diameters, combined in part, or all together.

Yet another disadvantageous aspect of the conventional staplers is the post-operative imaging challenges created by the presence of permanent metal staples left behind in the body. The present invention solves this problem by optionally using biocompatible materials such as non-stainless steels, or other malleable metals or absorbable plastics, which will safely biologically disintegrate over time, thereby eliminating any issue of disrupting the unobstructed imaging of organs at a future time via methods such as X-ray, MRI, ultrasound, or CT scans.

Other disadvantageous aspects of the conventional circular relate to opening and removing the device smoothly from the patient and knowing the position that is safe to open the device. The difficulty of removing a device after firing it or opening it to a position inadequate for safe removal can cause inadvertent tearing and undetected disruption of a portion of the staple line due to inability of the knife to cut completely through tissue and previous staple lines, and also due to the knife being retracted immediately after firing, and allowing the tissue to fall axially inward, causing it to snag on the edges of the cartridge and anvil. The present invention solves this problem by leaving the knife distal until opened further following withdrawal from the patient, and then retracting the knife sequentially thereafter, to prevent exposure to the clinicians during tissue doughnut inspection. Further, the present invention utilizes a hardened knife to effectively cut through prior staple lines, elimination of the break washer used in many circular surgical staplers today—replacing it with a more solid substrate for the cutting knife, and an automatically opening anvil to ensure the device is adequately opened to remove it safely without disrupting the anastomotic staple line.

Therefore, there exists a previously unappreciated need for a new and improved circular surgical stapler that facilitates the functionalities mentioned above and addresses the shortcomings of the prior art, as well as a broader invention that improve the ease of manufacture, and reduces the cost to manufacture ALL surgical stapling devices while simultaneously enhancing reliability and usability. It is to these ends that the present invention has been developed.

SUMMARY OF THE INVENTION

The present subject matter envisages a new simplified version of a surgical stapler. The surgical stapler comprises a body having a distal end and a proximal end. In the primary embodiment comprising a circular stapler, a first knob and a second knob is configured adjacent the proximal end of the body, with the distal end comprising a head comprising, but is not limited to a circular configuration. In the circular stapler configuration, an anvil and trocar assembly is configured adjacent the distal end of the surgical stapler, wherein the anvil and trocar assembly is coupled to the first knob, and the first knob is configured to facilitate the extension and retraction of the anvil and trocar assembly at the distal end of the body. A staple and knife assembly is configured adjacent the anvil and trocar assembly within the body, wherein the staple and knife assembly is coupled to the second knob, and wherein the second knob is configured to sequentially facilitate the firing of staples, and then the actuation of a knife to cut tissue.

In accordance with a non-limiting embodiment of the present subject matter, an aspect of the anvil and trocar assembly comprises at least one contiguous groove for receiving staples therein, for facilitating the stapling of required tissue. In the present embodiment of a circular stapling device, a knife abutment substrate is also situated on the anvil for receiving the knife, and to facilitate the cutting of tissue after stapling. In one or more embodiments of the stapler, no splines are necessary for radially aligning the anvil, as has been the case in virtually all conventional circular staplers on the global market.

In accordance with a non-limiting embodiment of the present subject matter, the surgical stapler further comprises a variable threaded member disposed within and coupled to the first knob and extending into the interior space. In one or more embodiments, an adjustable shuttle is configured for insertion and movement along a longitudinal axis of the variable threaded member, wherein the adjustable shuttle is coupled to the variable threaded member via a pin configured to engage with the variable thread to facilitate linear movement of the adjustable shuttle within the variable threaded member. A closure rod extends from the adjustable shuttle extending up to the distal end of the body.

In accordance with a non-limiting embodiment of the present subject matter, the anvil and trocar assembly comprises a trocar coupled to the closure rod, wherein rotation of the first knob facilitates rotation of the variable threaded member, which in turn facilitates the linear movement of the adjustable shuttle and the closure rod to facilitate extension and retraction of the trocar at the distal end of the body. In one embodiment, the anvil is configured for snap fitment onto the trocar.

In accordance with a non-limiting embodiment of the present subject matter, the surgical stapler further comprises a threaded pusher disposed within the body and coupled to the second knob, wherein the second knob includes an extension extending into the interior space of the body, and the extension includes a threaded pusher pin in engagement with threads configured on the threaded pusher.

In accordance with a non-limiting embodiment of the present subject matter, the surgical stapler further comprises a knife pusher driver disposed within the body adjacent the distal end and coupled to the threaded pusher.

In accordance with a non-limiting embodiment of the present subject matter, the surgical stapler further comprises a staple driver disposed adjacent the knife pusher within the body, wherein the knife pusher driver and the staple driver are configured to facilitate a consistently sequential firing of staples by the staple driver, and then the actuation of the knife by the knife pusher driver.

In accordance with a non-limiting embodiment of the present subject matter, the surgical stapler further comprises a firing safety assembly, wherein the firing safety assembly includes a firing safety tab configured on the second knob within the body. In one or more embodiments, a firing safety link is disposed adjacent the extension within the body, the firing safety link is configured to abut the firing safety tab, wherein the firing safety link abuts the firing safety tab on being displaced in the body towards the proximal end of the body, wherein the displacement of the firing safety link is facilitated by a guide pin extending from the adjustable shuttle.

In accordance with a non-limiting embodiment of the present subject matter, the surgical stapler further comprises an automatic open button provided on the proximal end of the first knob and configured for breaking the coupling, thereby optionally and selectively disengaging the first knob from the variable threaded member.

In accordance with a non-limiting embodiment of the present subject matter, the surgical stapler further comprises a first biasing element placed in the variable threaded member for providing a biasing force against the adjustable shuttle.

In accordance with a non-limiting embodiment of the present subject matter, the surgical stapler further comprises a second biasing element disposed between the trocar and the closure rod for providing a biasing force against the trocar.

An anvil for a surgical stapler is also envisaged herein. The anvil comprises a plurality of grooves for receiving staples therein subsequent to being fired for facilitating the stapling of required tissue, and a knife abutment substrate configured and mounted on the anvil.

The present invention described and detailed herein eliminates the need for discrete pockets to form staples, while simultaneously making the device easier to effectively use and fire, and also enhancing manufacturing reliability. Using simple grooves for staple formation, combined with a high-density staple pattern enabled by the grooves, leaks and vascular oozing are virtually eliminated, effectively providing improved hemostasis and less potential for leakage from hollow organs into the peritoneal cavity or other areas where leakage would be harmful to a patient. Moreover, there is a distinct clinical advantage in that without the need for high-precision critically-located pockets, the final staple forms produced are actually more consistent and symmetrical, due to eliminating the potential for misalignment between the staple housing and anvil pocket inclines, which misalignment occurs to some degree in virtually all currently marketed devices, due to manufacturing variances, and dimensional tolerance stackups among multiple fitted components, and clearance requirements when making or assembling the components.

Further, the simplified anvil embodied by the present invention is more reliably produced at a greatly reduced cost due to the lack of critical dimensions, reduced number of complicated manufacturing processes and machining, including no need for splines or ribs to be machined or molded onto the shaft of the anvil, or its mating components. The simpler manufacturing methods, no requirement for radial orientation of the anvil, and the groove patterns (versus discrete staple tip receiving pockets) further enable a wide variety of staple sizes and spacing variations in the staple cartridge, while using the same low cost anvil, thereby providing universal compatibility with a variety of staple cartridges and staple line adaptations, without, in many surgical stapler device configurations, changing out or discarding the expensive parent device and/or its mating anvil.

Another aspect of the present invention, particularly in a circular stapler configuration and embodiment, is the use the release of mechanically stored energy to provide automatic tissue release from the jaws of the device, by simply pressing a button upon completion of the firing sequence, after which action, the device automatically opens under spring bias to a position suitable for easy and safe device removal from the operative site, without disrupting the staple line and damaging the anastomosis.

Another aspect of the present invention is the use of a handle-mounted sound and tactile mechanism to provide clear feedback to clinicians, indicating staple form completion and tissue cutting completion, versus the current feedback method used in most currently available circular devices, which involve an explosive bursting of a circular knife edge through a plastic ring, and which is located inconveniently deep in the operative site during the cutting process; often the pelvis, abdomen, or other body cavity where the tactile feedback is muffled.

Another aspect of the present invention is the use of high mechanical advantage rotational knob coupled to a threaded screw and follower, as the means for actuating the staple forming and cutting functions of the device to prevent misfiring or incomplete firing of the device, which is known to result in patient harm or death if incompletely fired using many currently available devices.

Another aspect of the present invention is the use of a handle-mounted tissue pressure limiting device operatively in line with the tension drive train to mitigate the risk of tissue damage, properly setting the end effector gap to achieve the ideal healing pressure range prior to firing the staples, and thereby eliminating any need for surgeons to choose a device that provides a pre-chosen staple height, optionally deploying staples of varying staple height in the same firing, or to set the device in advance to said prescribed staple height, which most surgeons have difficulty determining, as the staple height determination is largely very subjective and ambiguous. The current method is for clinicians to visually observe the tissues, which can be technique and judgment-sensitive, vastly variable, highly consequential to a patient's health and recovery time, the success or failure of the procedure, and is therefore a large source of ambiguity and concern for clinicians.

Another aspect of the present invention is the integration of tiny gripping teeth located on the anvil surface that contacts tissue, which teeth may be etched, scribed, forged, deposited, coated, blasted with abrasive particulates, or machined to modify or texture the surface of the anvil for effective gripping of tissue, and which prevents tissue from migrating or slipping during the stapling and cutting processes.

Another aspect of the current invention is to utilize a hardened material for the knife, combined with a solid semi-rigid backstop substrate versus a break washer, to prevent oil-canning of the break washer as currently occurs, and which is especially consequential when cutting through prior staple lines that are sometimes present. Such instances can cause incomplete cutting of the staples and subsequent wedging of the damaged staples between the knife and the cartridge housing, which in turn causes the device to be attached to the operative site and newly-stapled tissue; even disrupting the anastomosis during removal and causing patient harm or death due to staple line leakage, which can go undetected by the clinician, or be discovered only when after adverse post-operative events occur, and which adverse events can result in a colostomy.

Another aspect of this invention is the inclusion of malleable metal staples, which contain pre-bent (slightly buckled in strategic locations) staple legs and optionally heat treated to produce selective locations of ultra-malleability, to affect a predictable buckling and subsequent forming of the staple legs into the desired B shape or other desirable folded shape, without the need for inclined staple ramps in the anvil to impart the initial bending direction. The pre-bent shapes essentially comprise an angular kink in the leg, which effectively weakens the staple legs to ensure the leg forming always occurs in a predictable direction, in this case with the tips of the staples biased toward each other to ensure a reliable and atraumatic B formation as the final staple shape. The staples can be made of a variety of metals, including titanium, stainless steel, and non-stainless materials such as zinc, aluminum, or non-stainless steels, or bio-absorbable plastics, which can essentially disintegrate over time, eliminating the issues surrounding image distortion, staple migration, infection, or other issues associated with foreign bodies left in place in the body. Further, the staple legs may have the bending behaviors altered by selective hardness differentials enabled by either heat treating or selectively altering the cross sections of the staple wire diameters to control the behaviors of the bending.

Another aspect of the invention is to employ a cartridge having pockets that are slightly positionally angled such that the legs of the staples, after piercing the tissue, then enter the corresponding anvil pockets having dual grooves, at prescribed locations to bias one leg of the staple one a particular side of the staple crown, and the opposite leg on the other side of the crown, to ensure a symmetrically formed staple, one leg on each side of the crown. Combined with the aspects described above, the resulting staple form results in a staple having legs that reverse completely, but rather generally do not recurve completely to a position perpendicular to the crown, thereby creating a hemostatic staple configuration.

Another aspect of this invention is to employ an ultra-low friction surface on the staple forming surface of the anvil, to ensure there is no binding or dragging of the staple tips against the anvil forming surface, which could impede movement of the tips during staple formation, and potentially cause malformation of the staples. Such low friction surfaces can be implemented by coating the metal anvil with low friction lubricants, either dry lubricants, or may comprise conformably coated lubricious liquids or gelatinous substances, or such coatings that carry suspended lubricious particles of flakes such as polytetrafluoroethylene (PTFE), greases, oils, or surfactants such as sodium stearate or other forms of slippery soaps to provide a surface that causes the staple tips to easily slide toward one another in a predictable way. Another method of coating the anvils is to electroplate or otherwise coat or bake onto the surface or construct the anvil with low friction materials such as lubricious metals, and ones that are ideally molecularly dissimilar to the metal staples being formed.

The above summary contains simplifications, generalizations and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 1A through FIG. 1D illustrate views of a circular surgical stapler in unactuated states and actuated states, in accordance with embodiments of the present subject matter.

FIG. 7A illustrates a perspective view of the anvil, in accordance with embodiments of the present subject matter.

FIG. 10C illustrates a schematic view of a staple guide, in accordance with another embodiment of the present subject matter.

FIG. 11A and FIG. 11B illustrates views of an anvil and grooves configured on the anvil, in accordance with an embodiment of the present subject matter.

FIG. 12A and FIG. 12B illustrates views of an anvil and grooves configured on the anvil, in accordance with an embodiment of the present subject matter.

FIG. 16A and FIG. 16B illustrate schematic views of an anvil having a grooveless configuration, in accordance with an embodiment of the present subject matter.

DETAILED DESCRIPTION OF EXAMPLE EMBODIMENTS

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon.

Moreover, to the extent that spatial terms such as "top," "bottom," "upper," "lower," "vertical," "horizontal," are used herein with reference to the drawings, it will be appreciated that such terms are used for exemplary description purposes only and not intended to be limiting or absolute. In that regard, it will be understood that surgical instruments such as disclosed herein may be used in orientations and positions not limited to those shown and described herein.

In addition, the term "endoscopic" is used generally to refer to surgical procedures performed through a small incision or a cannula inserted into a patient's body including endoscopic, laparoscopic, and arthroscopic surgical procedures. Finally, the term clinician is used generally to refer to medical personnel including doctors, nurses, and support personnel.

Figure 1A:
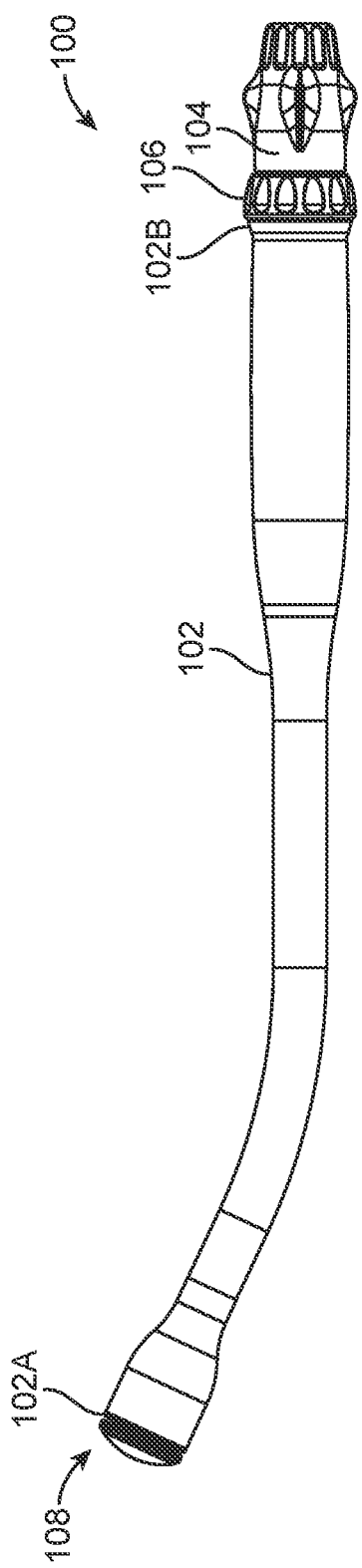
Figure 1B:
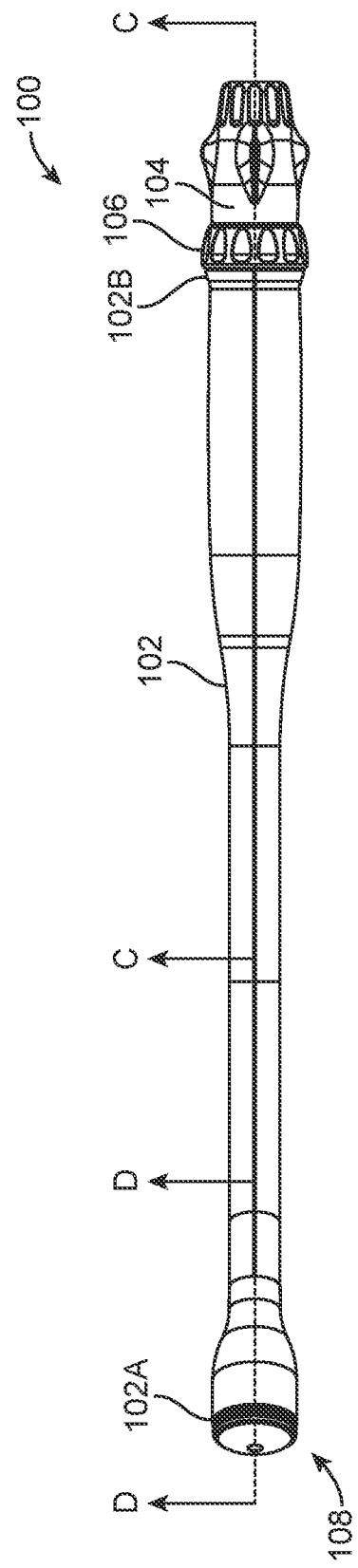

FIG. 1A through FIG. 1D illustrate views of a circular surgical stapler 100 (hereinafter interchangeably referred to as stapler 100 or surgical stapler 100) in unactuated states and actuated states. FIG. 1A and FIG. 1B illustrate unactuated views of the stapler 100, while FIG. 1C and FIG. 1D illustrate actuated views of the stapler 100. Reference hereinafter is directed to FIG. 1A through FIG. 1D. In accordance with an embodiment of the present subject matter, the stapler 100 comprises a body 102 having a distal end 102A and a proximal end 102B. The body 102 defines an interior space. A first knob 104 and a second knob 106 are configured adjacent the proximal end 102B of the body 102. More specifically, the second knob 106 is fitted at the proximal end 102B, and the first knob 104 is coupled to the second knob 106. An anvil and trocar assembly 108 is configured adjacent the distal end 102A of the surgical stapler 100, wherein the anvil and trocar assembly 108 is coupled to the first knob 104. More specifically, the first knob 104 is configured to facilitate the extension and retraction of the anvil and trocar assembly 108 at the distal end of the body 102. A staple and knife assembly (not seen in FIG. 1A through FIG. 1D) is configured adjacent the anvil and trocar assembly 108 within the body 102, wherein the staple and knife assembly is coupled to the second knob 106, and wherein the second knob 106 is configured to facilitate firing of staples and actuation of a knife of the staple and knife assembly sequentially. The sequential actuation of the staples and the knife of the stapler 100 are discussed in detail in the subsequent sections of the present disclosure.

Figure 2:
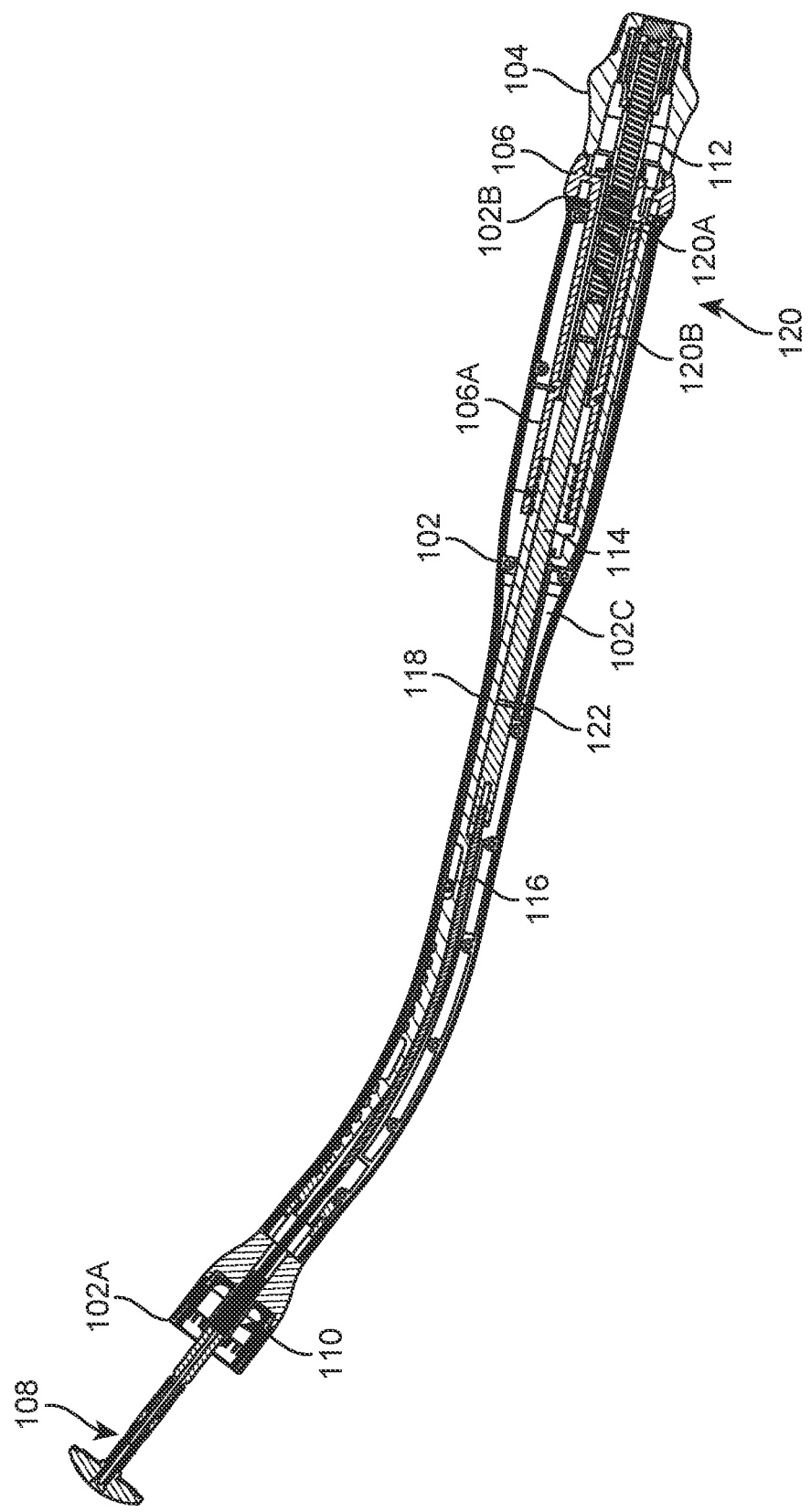
FIG. 2 illustrates a sectional view of the circular surgical stapler in the actuated state, in accordance with embodiments of the present subject matter.

FIG. 2 illustrates a sectional view of the circular surgical stapler 100 in the actuated state, in accordance with embodiments of the present subject matter. Referring to FIG. 2, the staple and knife assembly 110 is configured concentric to the anvil and trocar assembly 108 at the distal end 102A of the body 102. The body 102 defines an interior space 102C for body all the different components for transmission of the movements of the first and second knobs 104, 106 to the anvil and trocar 108 and the staple and knife assembly 110.

Referring to FIG. 2, the stapler 100 comprises a variable threaded tube 112 disposed within and coupled to the first knob 104 and extending into the interior space 102C. The stapler 100 further comprises an adjustable shuttle 114 disposed within the interior space 102C such that a portion of the adjustable shuttle 114 is accommodated within the variable threaded tube 112 and extends therefrom into the interior space 102C. The stapler 100 further comprises a closure rod 116 disposed within the interior space 102C such that a portion of the closure rod 116 is accommodated within the adjustable shuttle 114 and extends therefrom up to a location in the interior space near the distal end 102A. The anvil and trocar assembly 108 is coupled to the closure rod 116. More specifically, the extension and retraction of the anvil and trocar assembly 108 required for the operation of the surgical stapler 100 is facilitated by the linear movement of the closure rod 116. The details of the operation of the closure rod 116 and the extension and retraction thereof are discussed in the subsequent sections of the present disclosure.

Referring to FIG. 2, the surgical stapler 100 further comprises the second knob 106, wherein the second knob 106 includes an extension 106A that extends into the interior space 102C. The surgical stapler 100 further comprises a threaded pusher 118 coupled to the extension 106A and extending into interior space 102C of the body 102 to a location near the distal end 102A. The rotation of the second knob 106 facilitates the linear movement of the threaded pusher 118, which in turn facilitates the firing of the staples and the actuation of the knife sequentially. The details of the sequential firing of the staples and the actuation of the knife via the rotation of the second knob 106 is discussed in more detail in the subsequent sections of the present disclosure.

Referring to FIG. 2, the surgical stapler 100 further comprises a firing safety assembly 120, wherein the firing safety assembly 120 includes a firing safety tab 120A configured on the second knob 106 within the body 102. The firing safety assembly 120 further comprises a firing safety link 120B disposed adjacent the extension 106A within the body 102. The firing safety link 120B is configured to abut the firing safety tab 120A, wherein the firing safety link 120B abuts the firing safety tab 120A on being displaced in the body 102 towards the proximal end 102B of the body. The displacement of the firing safety link 120B is facilitated by a guide pin 122 extending from the adjustable shuttle 114.

Figure 3A:
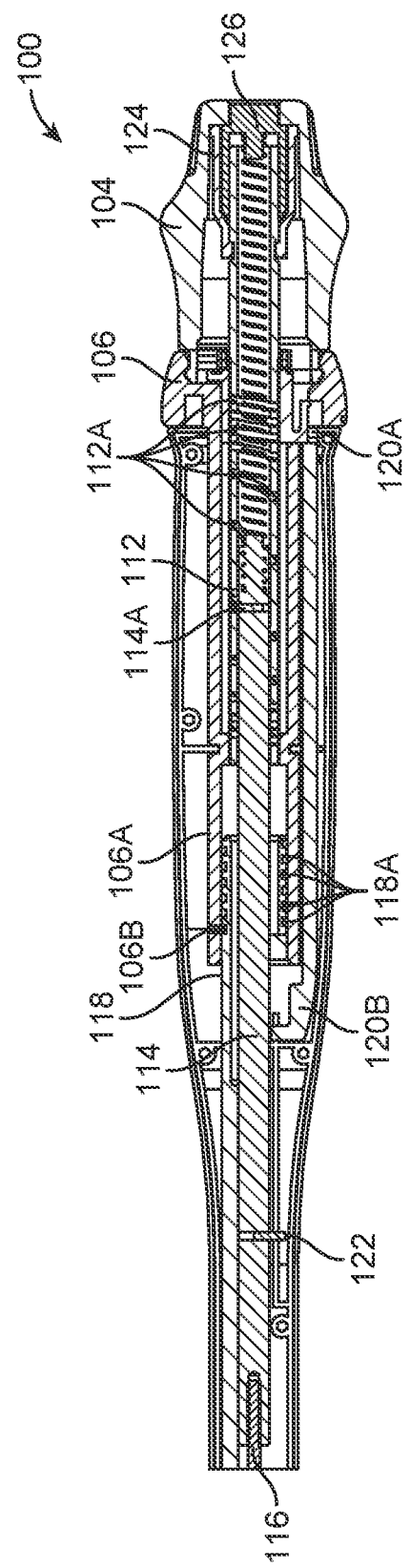
FIG. 3A through FIG. 3C illustrate sectional views of the circular surgical stapler along section line A-A of FIG. 1C depicting the operation of actuation of the circular surgical stapler, in accordance with embodiments of the present subject matter.
Figure 3B:
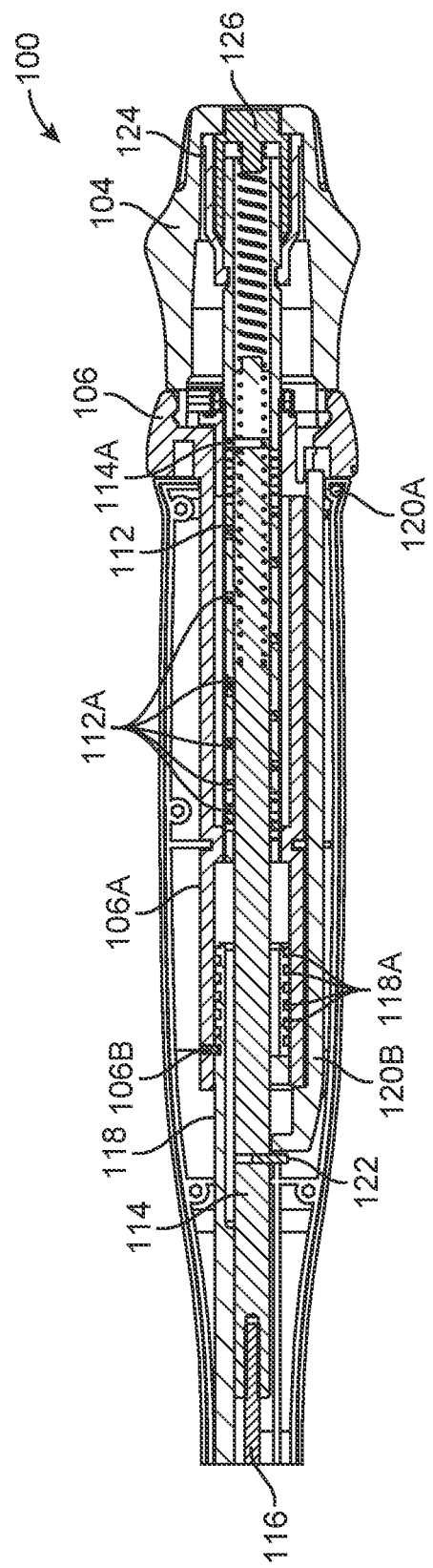
Figure 3C:
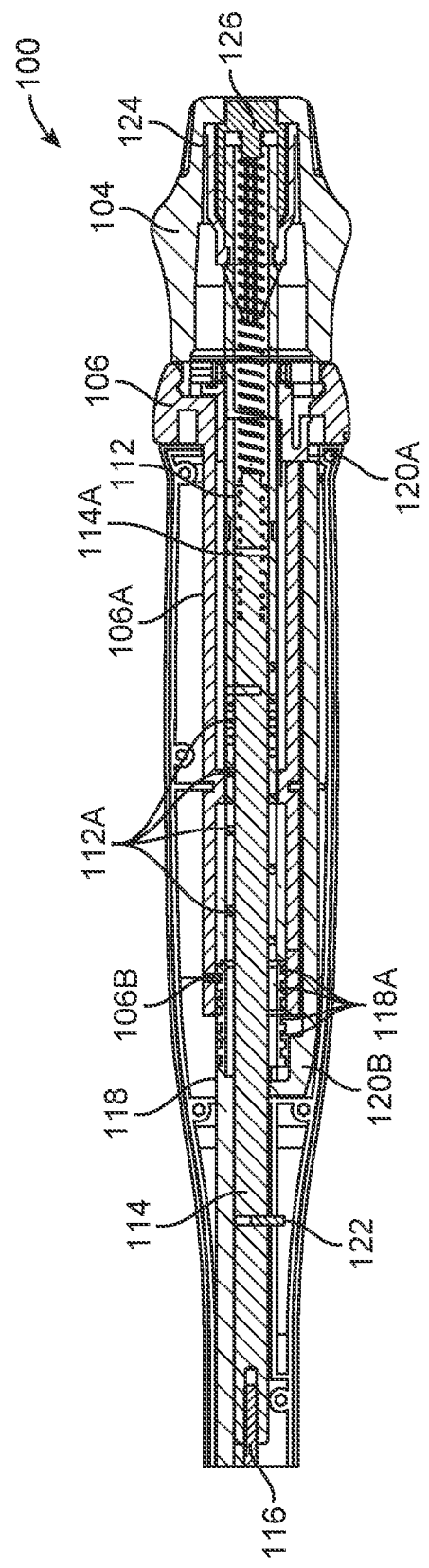

FIG. 3A through FIG. 3C illustrate sectional views of the circular surgical stapler 100 along section line A-A of FIG. 1C depicting the operation of actuation of the circular surgical stapler 100, in accordance with embodiments of the present subject matter. Referring to FIG. 3A, the first knob 104 is at its original rest position, i.e., the first knob 104 is at its initial position where it is yet to be rotated by a surgeon. In this position, the guide pin 122 is spaced apart from the firing safety link 120B. As such, the firing safety link 120B is also in an at-rest position where it does not apply any kind of force onto the firing safety tab 120A, and therefore, the firing safety tab 120A keeps the second knob 106 locked, thereby preventing any accidental actuation of the staple and knife assembly 110.

Reference is now directed to FIG. 3B. As seen in FIG. 3B, the guide pin 122 is displaced and is contacting the firing safety link 120B. More specifically, the guide pin 122 urges the firing safety link 120B against the firing safety tab 120A, which then allows the rotation of the second knob 106. The movement of the guide pin 122 is facilitated by the rotation of the first knob 104. More specifically, the variable threaded tube 112 is coupled to the first knob 104 such that the rotation of the first knob 104 facilitates the rotation of the variable threaded tube 112. In accordance with one embodiment of the present subject matter, the aforementioned rotatable coupling between the first knob 104 and the variable threaded tube 112 may be facilitated via a snap fit element 124 disposed operatively between the first knob 104 and the variable threaded tube 112 in a manner that the snap fit element 124 is pressed against the variable threaded tube 112 by an auto open button 126 configured on the first knob 104. More specifically, the first knob 104 includes the auto open button 126 and the snap fit element 124 placed between itself and the variable threaded tube 112.

The variable threaded tube 112 defines a variable thread 112A along an inner surface thereof. The adjustable shuttle 114 is configured for insertion and movement along a longitudinal axis of the variable threaded tube 112, wherein the adjustable shuttle 114 is coupled to the variable threaded tube 112 via a pin 114A configured to engage with the variable thread 112A to facilitate the linear movement of the adjustable shuttle 114 within the variable threaded tube 112. More specifically, the pin 114A is in engagement with the variable thread 112A, and when the first knob 104 is rotated, the variable threaded tube 112 rotates as well. The rotation of the variable threaded tube 112 causes the pin 114A to follow the variable thread 112A in accordance with the direction of rotation of the first knob 104. In one embodiment, the clockwise rotation of the first knob 104 may facilitate the movement of the adjustable shuttle 114 towards the distal end of the body for facilitating the extension of the anvil and trocar assembly from the distal end of the body. Similarly, the counterclockwise rotation of the first knob 104 may facilitate the retraction of the anvil and trocar assembly. The closure rod 116 extends from the adjustable shuttle 114 up to the distal end of the body for facilitating the extension or retraction of the anvil and trocar assembly in accordance with the rotation of the first knob 104.

Referring to FIG. 3B, while the guide pin 122 urges the firing safety link 120B to depress the firing safety tab 120A, the surgeon can now rotate the second knob 106 as the firing safety tab 120A is depressed and can no longer lock the rotational movement of the second knob 106. As the surgeon rotates the second knob 106, the extension 106A of the second knob 106 also rotates. The rotation of the extension 106A facilitates the linear movement of the threaded pusher 118 that is coupled to the extension 106A. More specifically, the threaded pusher 118 includes threads 118A that are configured to be in engagement with a threaded pusher pin 106B configured on the extension 106A. As the second knob 106 is rotated, the extension 106A and the threaded pusher pin 106B rotate in accordance with the direction of rotation of the second knob 106. In accordance with one embodiment, the second knob 106 and the threaded pusher 118 may be configured such that a clockwise rotation of the second knob 106 facilitates the linear movement of the threaded pusher 118 towards the distal end of the body, thereby facilitating the actuation of the staple and knife assembly.

Referring to FIG. 3C, the operation of the auto open button is depicted. The operation of the auto open button is explained in the subsequent sections of the present disclosure.

Figure 4A:
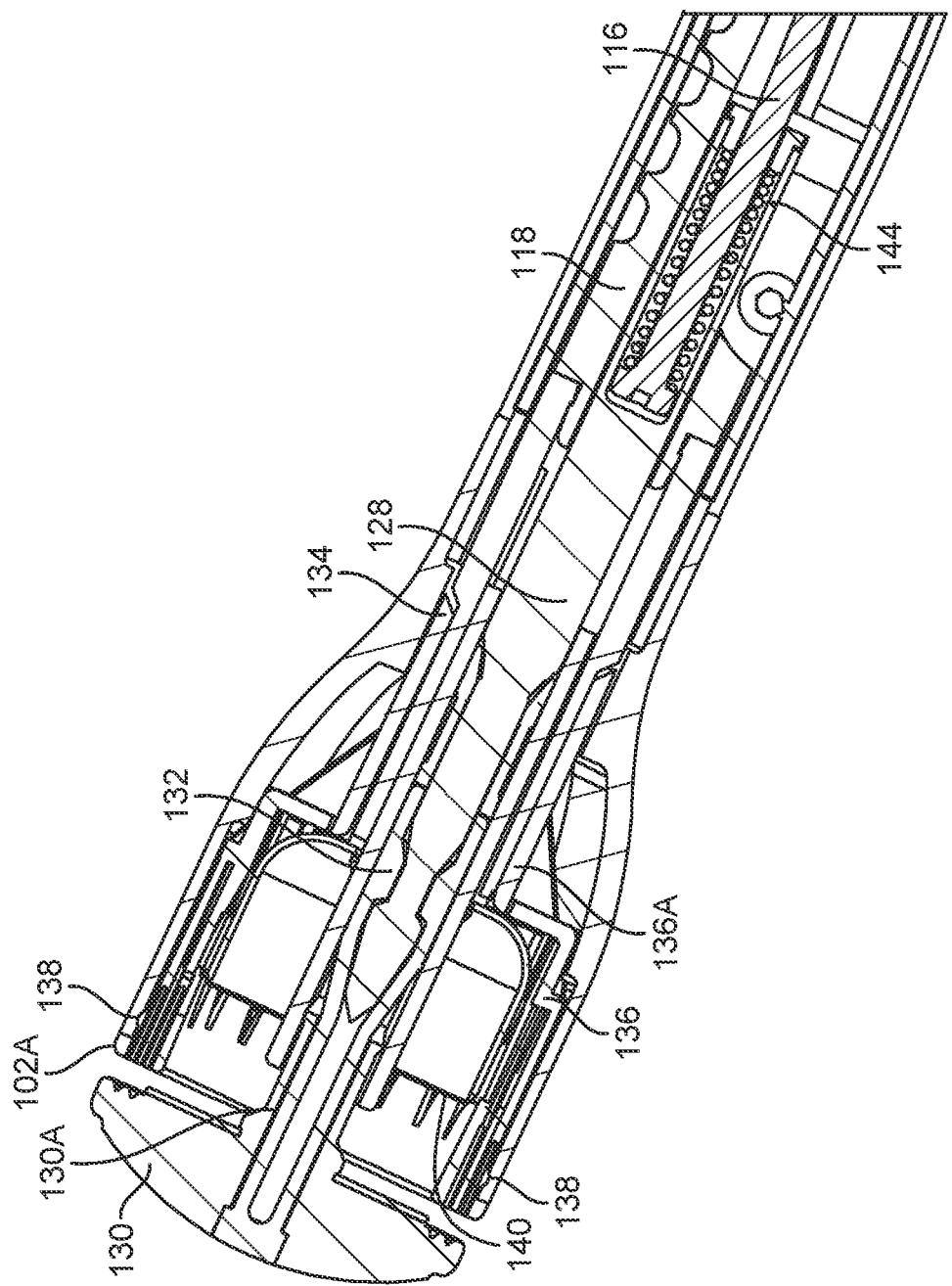
FIG. 4A through FIG. 4H illustrate sectional views of the circular surgical stapler along section lines B-B and D-D depicting the operation of anvil and trocar assembly of the circular surgical stapler, in accordance with embodiments of the present subject matter.
Figure 4B:
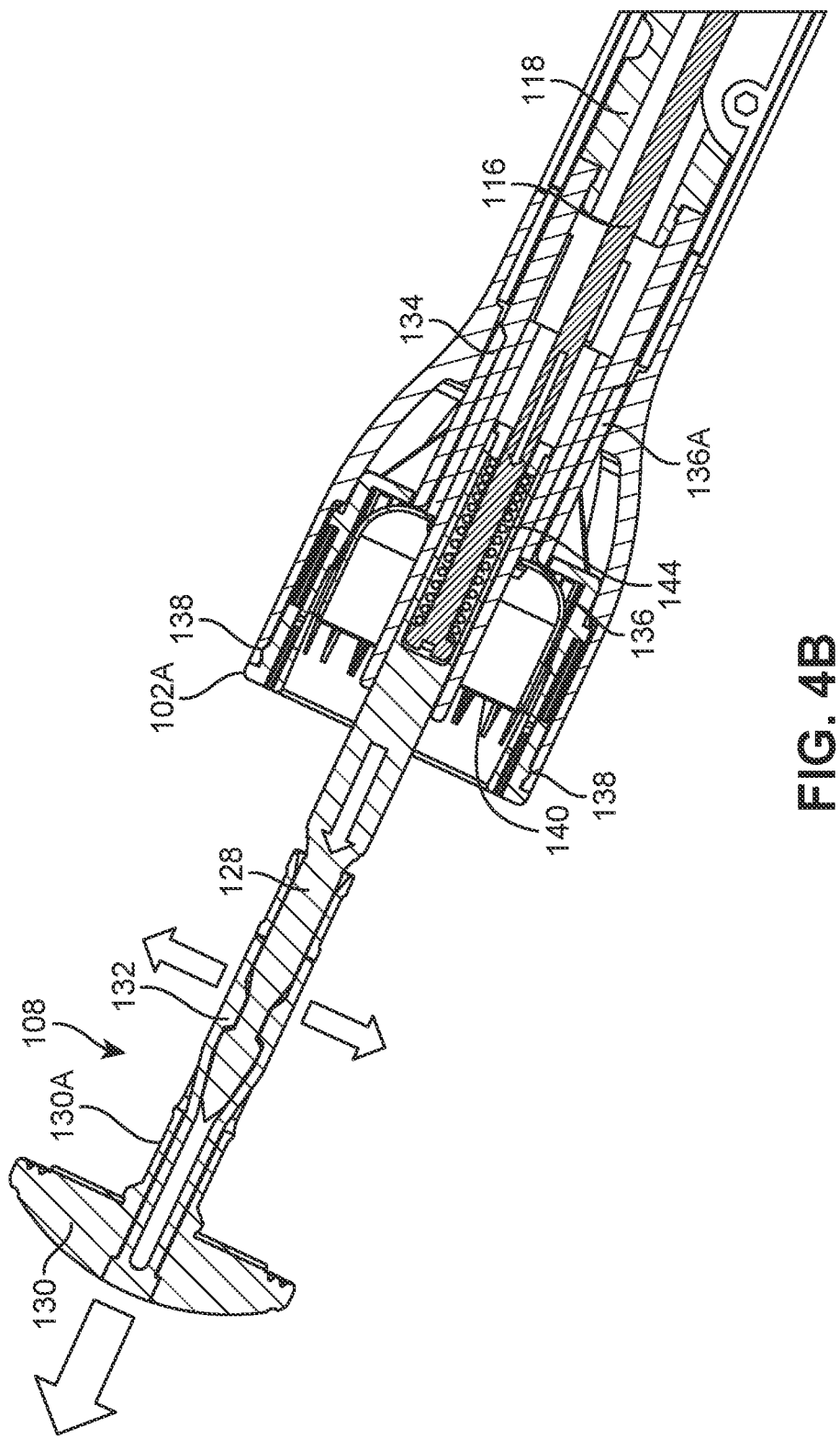

FIG. 4A through FIG. 4H illustrate sectional views of the circular surgical stapler 100 along section lines B-B and D-D depicting the operation of anvil and trocar assembly of the circular surgical stapler 100, in accordance with embodiments of the present subject matter. Referring to FIG. 4A, the anvil and trocar assembly 108, in accordance with an embodiment of the present subject matter, comprises a trocar 128 coupled to the closure rod 116, wherein rotation of the first knob 104 facilitates rotation of the variable threaded tube 112, which in turn facilitates linear movement of the adjustable shuttle 114 and the closure rod 116 to facilitate extension and retraction of the trocar at the distal end 102A of the body 102. In one embodiment, the anvil is configured for snap fitment onto the trocar. As seen in FIG. 4B, the snap fitment between trocar 128 and anvil 130 is facilitated via a clip 132 configured in a hollow extension 130A of anvil 130.

Referring back to FIG. 4A and FIG. 4B, the staple and knife assembly 110, in accordance with an embodiment of the present subject matter, comprises a knife pusher driver 134 disposed within the body 102 adjacent the distal end 102A and coupled to the threaded pusher 118. More specifically, the knife pusher driver 134 is configured to move linearly within the body in accordance with the movement of the threaded pusher 118. The staple and knife assembly no further comprises a staple driver 136 disposed adjacent the knife pusher driver 134 within the body 102, wherein the knife pusher driver 134 and the staple driver 136 are configured to facilitate firing of staples 138 by the staple driver 136 and actuation of a knife 140 by the knife pusher driver sequentially. More specifically, the staples 138 are configured in a more advanced position relative to the knife 140, and the knife pusher driver 134 that is pushed by the threaded pusher 118 in turn pushes the staple driver 136, thereby facilitating the firing of staples 138. Subsequent to the firing of staples 138, the knife pusher driver 134 facilitates the actuation of the knife 140.

Figure 4C:
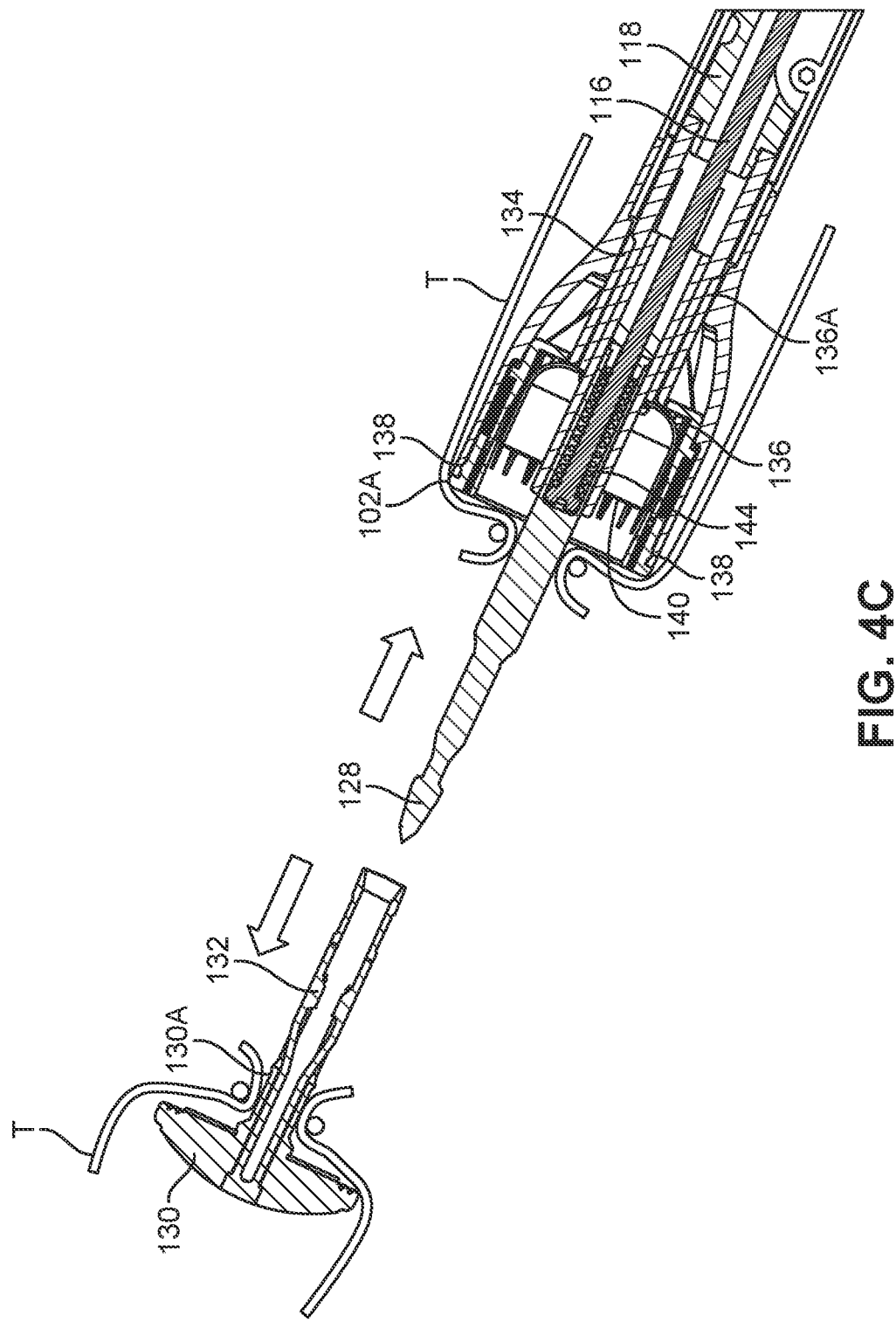

Referring to FIG. 4C, the operational view of the stapler 100 at the distal end of the body 102, is illustrated. In operation, the anvil 130 is removed from the trocar 128. The anvil 130 and the trocar 128 have the tissues T that need to be joined purse stringed thereto.

Figure 4D:
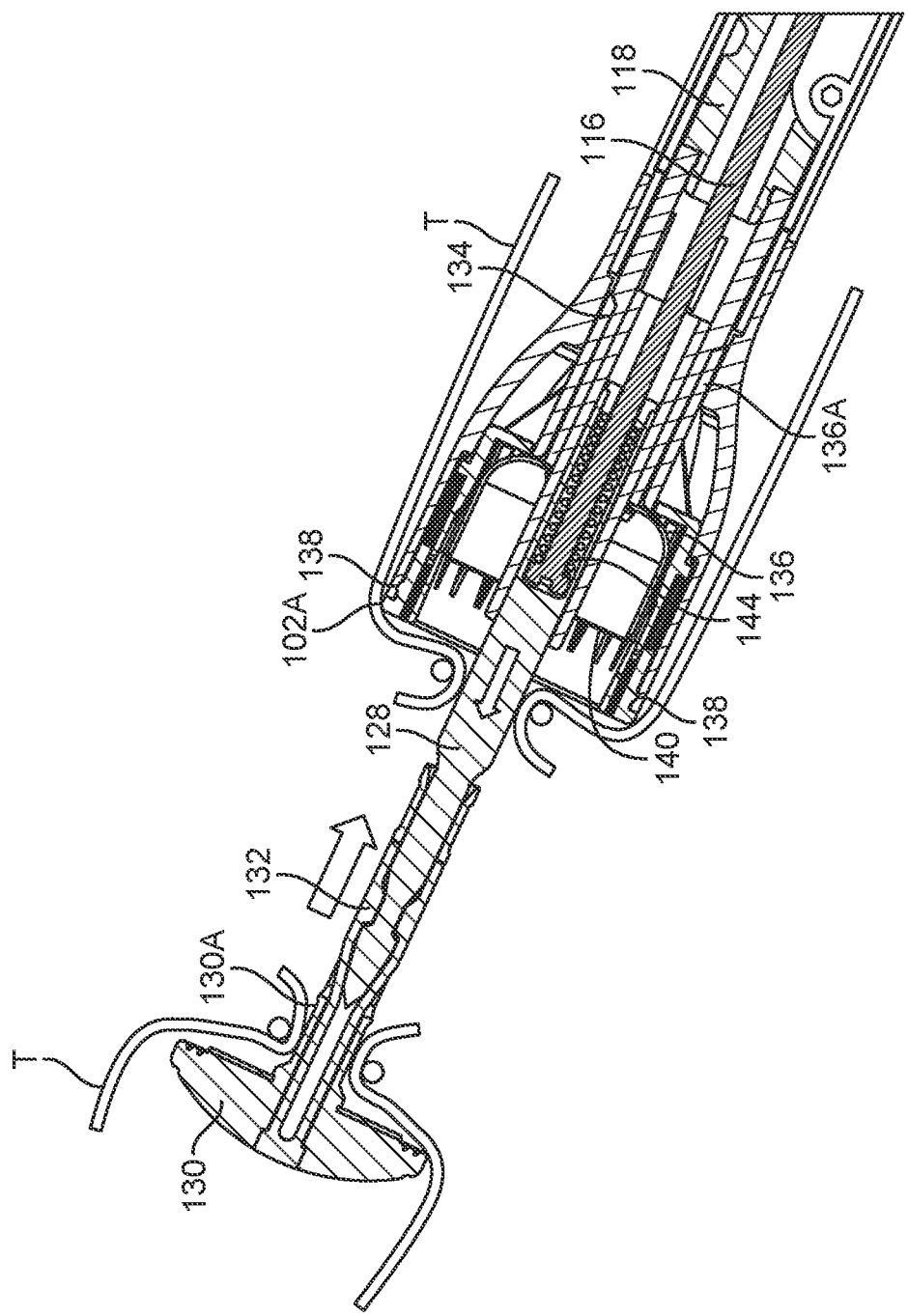

Referring to FIG. 4D, trocar 128 and the anvil 130 are assembled together, wherein the clip 132 configured within the hollow extension 130A of the anvil 130 facilitates a snap fitment between the trocar 128 and the anvil 130.

Figure 4E:
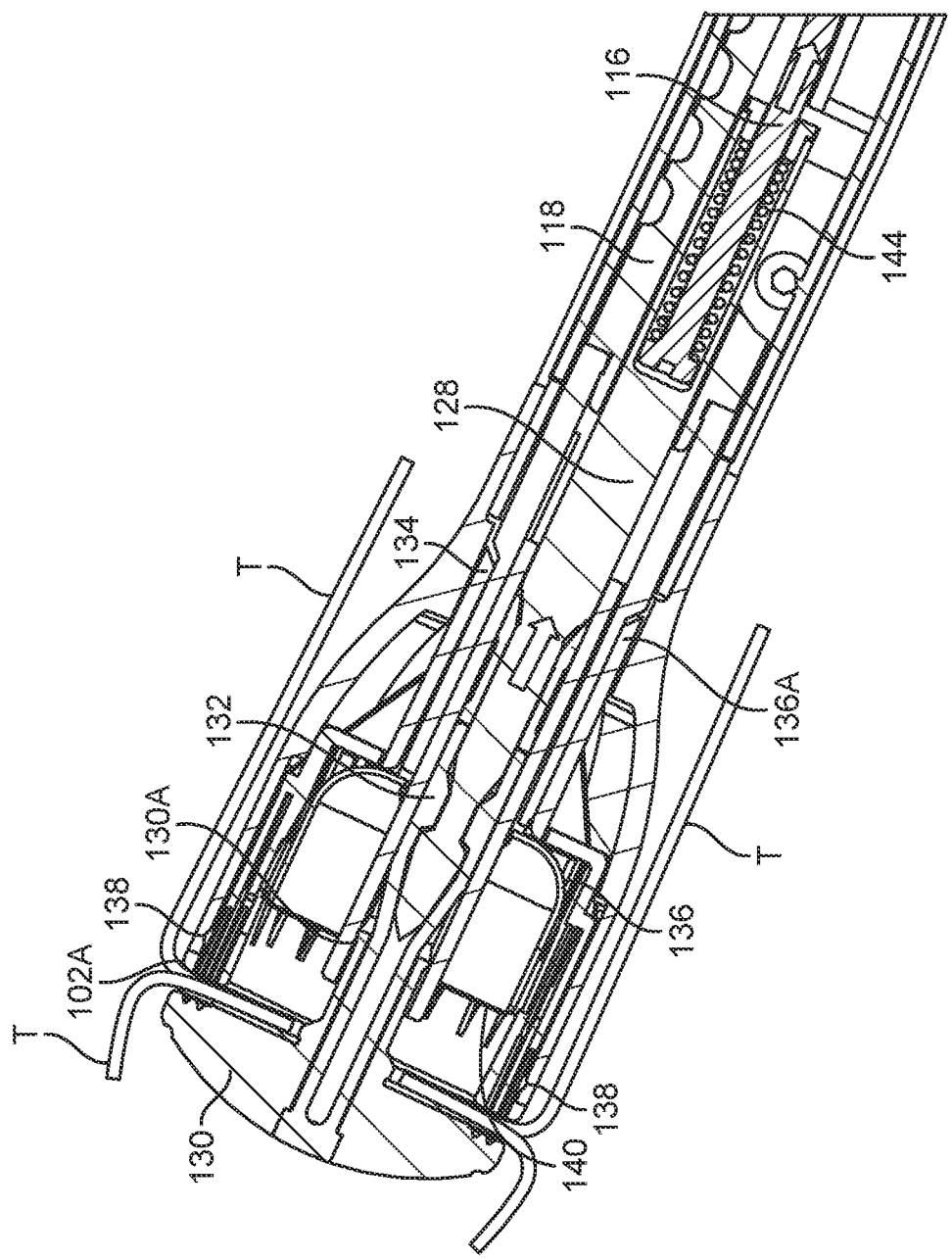

Referring to FIG. 4E, the anvil 130 and the trocar 128 are retracted. In accordance with an embodiment of the present subject matter, the extension and retraction of the anvil 130 and the trocar 128 are affected via the rotation of the first knob. More specifically, the rotation of the first knob facilitates the rotation of the variable threaded tube, and the rotation of the variable threaded tube facilitates the linear movement of the adjustable shuttle and the closure rod, thereby causing the extension or retraction of the trocar 128. In accordance with one embodiment of the present subject matter, the clockwise rotation of the first knob facilitates retraction of the trocar 128, and the counterclockwise rotation of the first knob facilitates extension of the trocar 128. In this position, the tissues T are held securely under compression between the anvil 130 and the distal end 102A of the body.

Figure 4F:
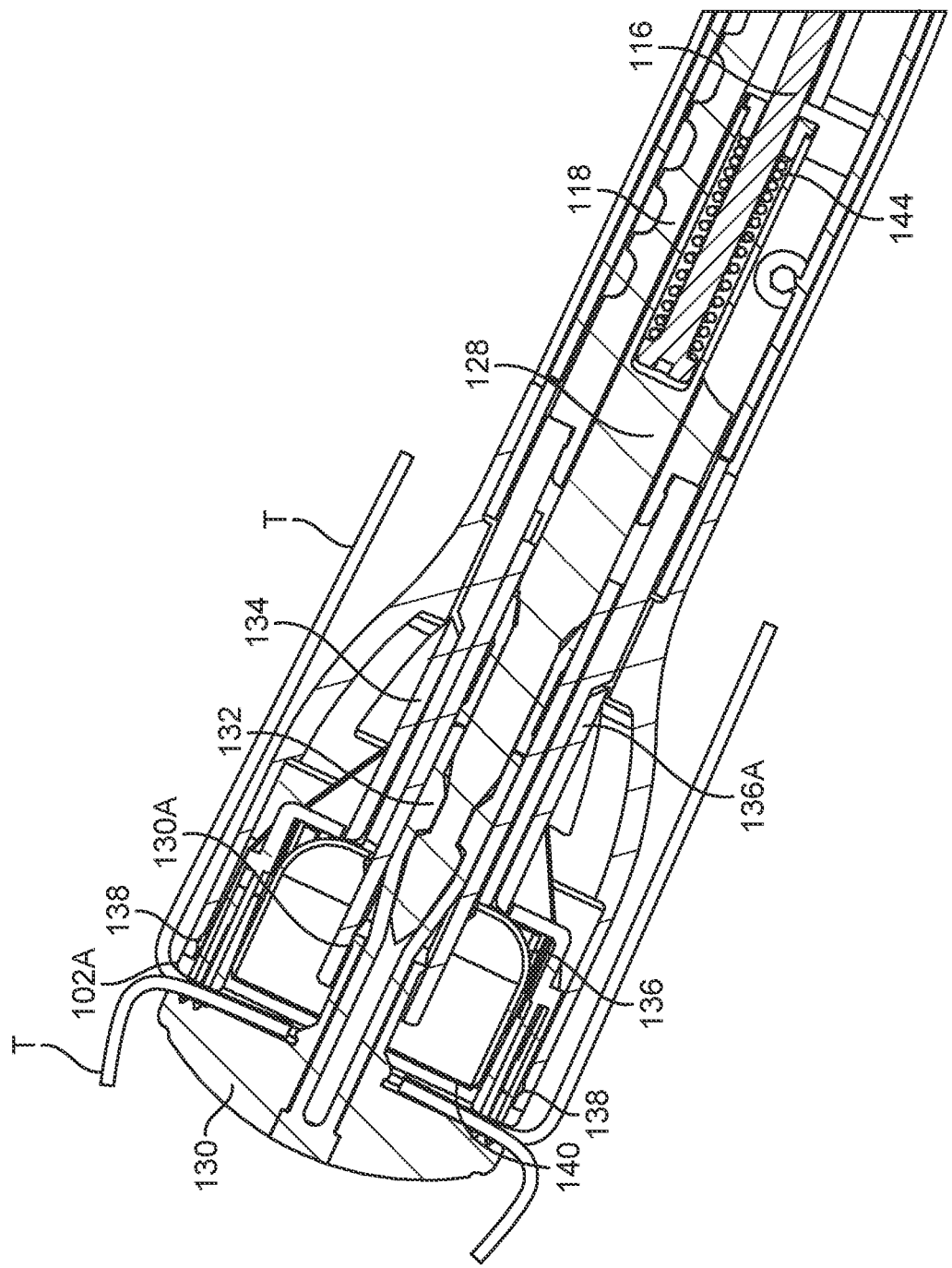

Referring to FIG. 4F, the second knob is rotated clockwise direction for facilitate the linear movement of the driver pusher driver 134, which in turn facilitates the linear movement of the staple driver 136 towards the distal end for facilitating the firing of the staples 138. The clockwise rotation of the second knob facilitates the linear movement of the threaded pusher 118 towards the distal end, thereby pushing the knife pusher driver 134 and the staple driver 136 to facilitate the firing of the staples 138.

Figure 4G:
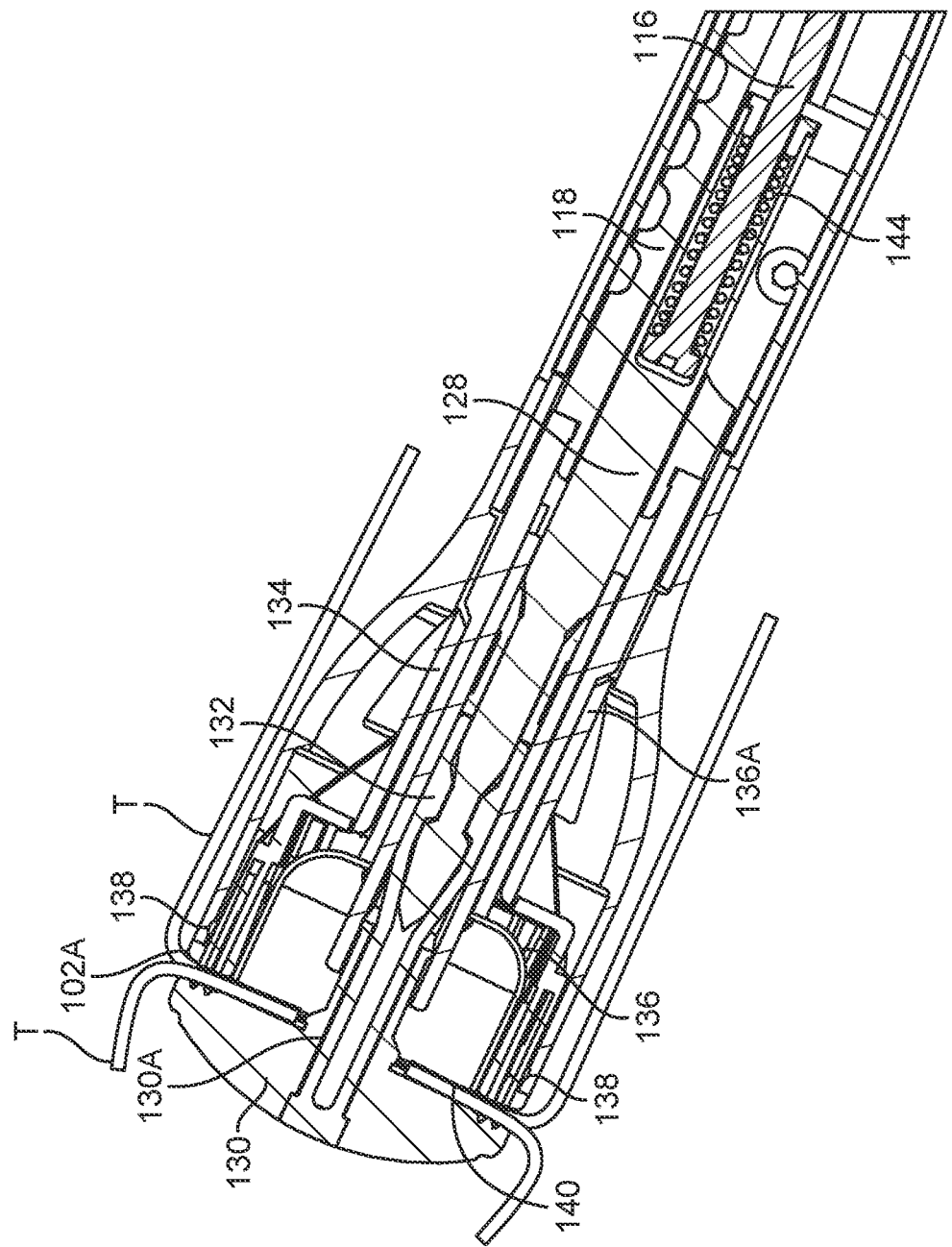

Referring to FIG. 4G, the second knob is rotated even more to facilitate the splaying of the tabs 136A of the staple driver 136 to facilitate easy movement of the knife pusher driver 134 by passing the staple driver 136, thereby pushing the knife 140 towards the tissues T that are held between the anvil 130 and the distal end 102A. At this stage, the stapling of the tissues T has already taken place in the previous step, and the knife 140 facilitates the cutting of the trapped tissue to obtain tissue doughnuts that are required to be inspected by the surgeon subsequent in whole operation. In one embodiment, an alert is provided to the surgeon once the stapling and cutting operations are completed via the stapler 100. In some embodiments, sensors may be used to sense the completion of the operation, and an alert in the form of an audio signal (e.g., a beep) or a visual signal (e.g., a light signal via an LED) may be provided to the surgeon. In some other embodiments a click sound is heard once the knife 140 contacts the anvil 130

Figure 4H:
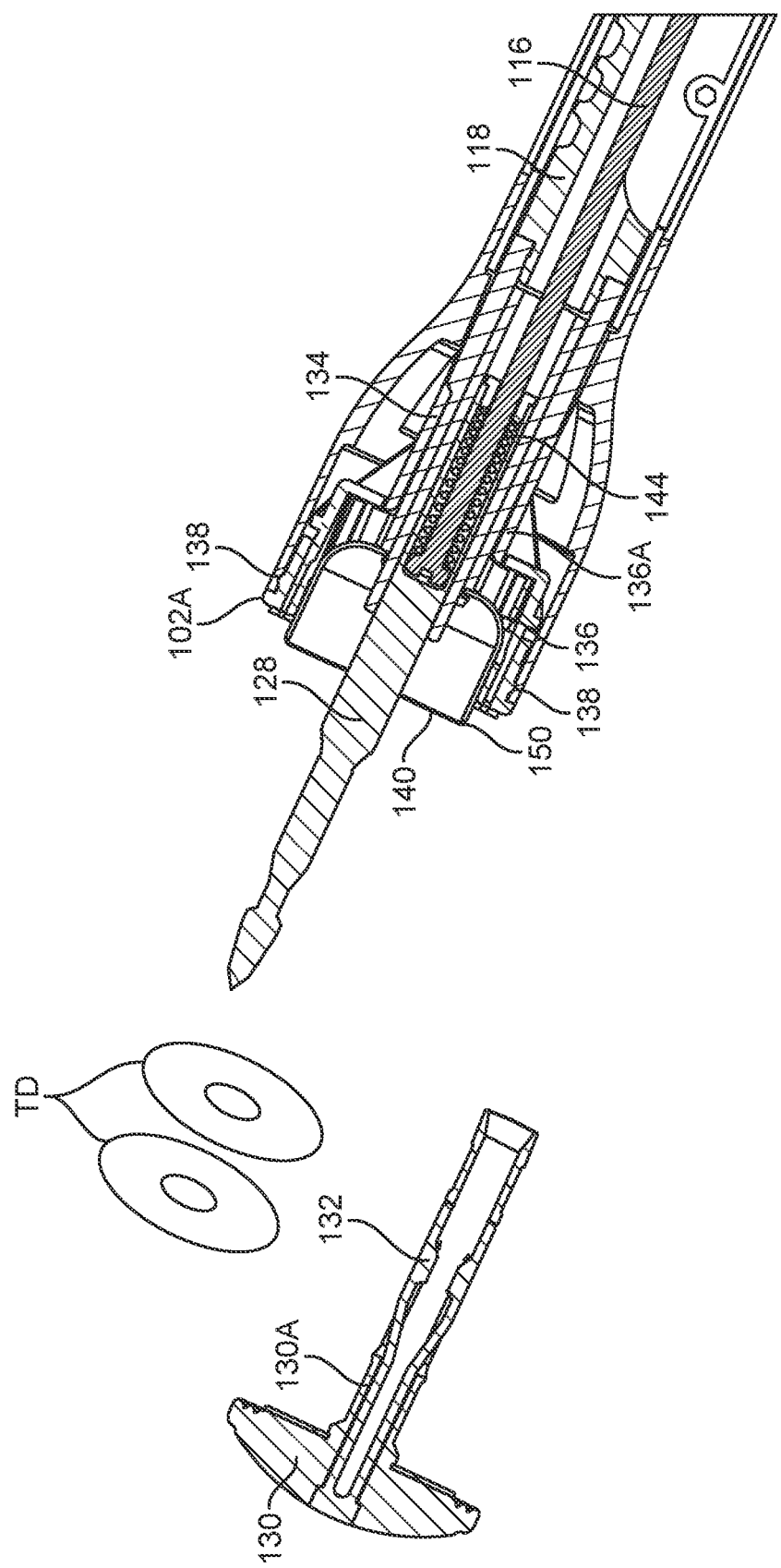

Referring to FIG. 3C and FIG. 4H, the auto open button 126 is pressed subsequent to the completion of the stapling and tissue cutting operation. Once the auto open button 126 is pressed, the snap fit element 124 is spread apart, thereby releasing the variable threaded tube 112 from the being engaged to the first knob 104. A first biasing element 142, disposed between the first knob 104 and the variable threaded tube 112, urges the variable threaded tube 112 away from the first knob 104 subsequent to the disengagement of the variable threaded tube 112 with the first knob 104. Once the variable threaded tube 112 disengages with the first knob 104, the trocar 128 and the anvil 130 are also displaced beyond the distal end 102A a bit, thereby ensuring that the tissue doughnuts TD are entirely separated from the joined tissues subsequent to the completion of the stapling and tissue cutting operation of the stapler 100. As seen in FIG. 4H, the stapler is then removed out of the patient's body, and the anvil 130 is separated from the trocar 128 to obtain the tissue doughnuts TD for analysis by the surgeon.

A disadvantageous aspect of the conventional circular relates to opening and removing the device smoothly from the patient and knowing the position that is safe to open the device. The difficulty of removing a device after firing it or opening it to a position inadequate for safe removal can cause inadvertent tearing and undetected disruption of a portion of the staple line due to inability of the knife to cut completely through tissue and previous staple lines, and also due to the knife being retracted immediately after firing, and allowing the tissue to fall axially inward, causing it to snag on the edges of the cartridge and anvil. The present invention solves this problem by leaving the knife 140 distal until opened further following withdrawal from the patient, and then retracting the knife 140 sequentially thereafter, to prevent exposure to the clinicians during tissue doughnut inspection. Further, the present invention utilizes a hardened knife to effectively cut through prior staple lines, and an automatically opening anvil to ensure the device is adequately opened to remove it safely without disrupting the anastomotic staple line.

It is to be noted that the surgical stapler further comprises a second biasing element 144 disposed between the trocar 128 and the closure rod 116 for providing a biasing force against the downward movement of the trocar 128 to limit the compressive forces acting on the tissues T held between the anvil 130 and the distal end 102A to prevent any unwanted tissue injury.

Figure 5C:
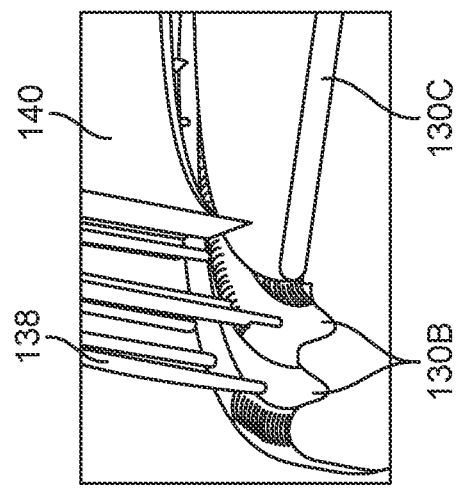
FIG. 5A and FIG. 5C illustrate views of the anvil, in accordance with embodiments of the present subject matter.
Figure 5B:
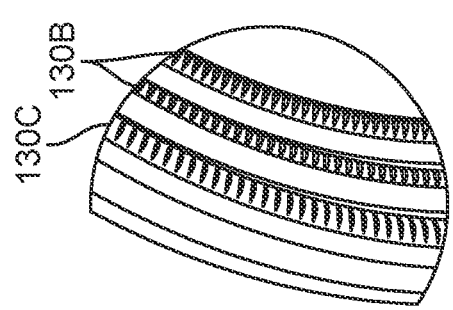

FIG. 5A and FIG. 5B illustrate views of the anvil 130, in accordance with embodiments of the present subject matter. The anvil 130, in accordance with an embodiment of the subject matter, comprises a pair of grooves 130B for receiving staples therein subsequent to being fired for facilitating the stapling of required tissue. A knife abutment substrate 130C is radially configured on the anvil 130 spaced apart concentrically from the pair of grooves 130B. In accordance with one embodiment, the pair of grooves 130B are radially extending grooves. In accordance with a non-limiting embodiment of the present subject matter, the knife abutment substrate 130C is configured as a third groove. In another embodiment illustrated in FIG. 5C, the knife abutment substrate 130C is configured as a separate layer. In one embodiment, the knife abutment substrate 130C is made from a biocompatible material. In accordance with one embodiment of the present subject matter, the anvil is constructed of stainless steel or aluminum metal that is anodized, treated, oxidized, or otherwise tinted with colors that deviate from the natural machined metal-colored finish. In another embodiment, the anvil is constructed of stainless steel or aluminum metal coated or impregnated with materials such as polytetrafluoroethylene (PTFE), stearate emulsions, or greases, which when interacting with the malleable metal staple, generate a coefficient of friction less than or equal to 0.5, whether static or sliding. In yet another embodiment, the anvil is constructed of polymer and then electro-plated or otherwise conformably coated or shielded with a layer of metal that is substantially hard enough to enable staples to form.

Figure 6A:
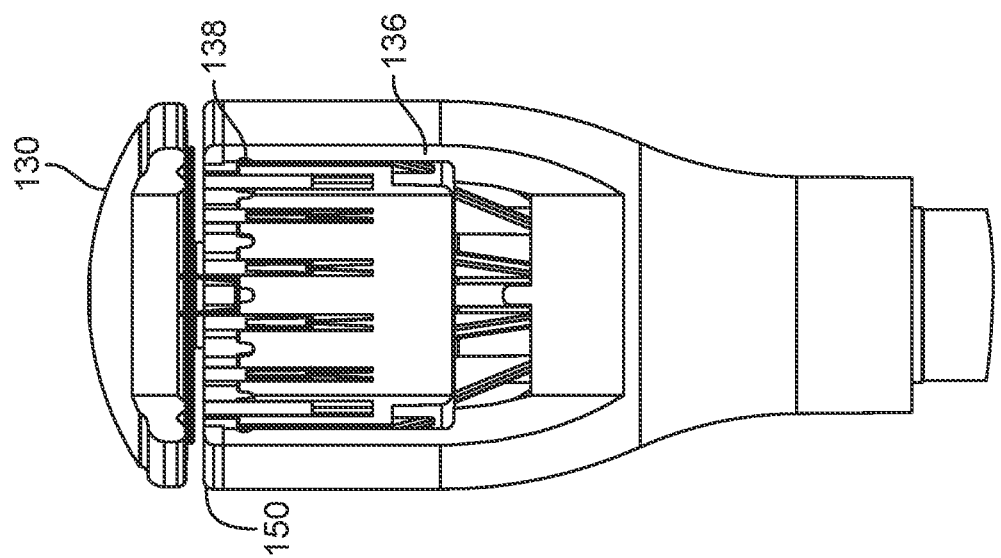
FIG. 6A through FIG. 6C illustrate views depicting the bending of staple subsequent to firing the circular surgical stapler, in accordance with embodiments of the present subject matter.
Figure 6B:
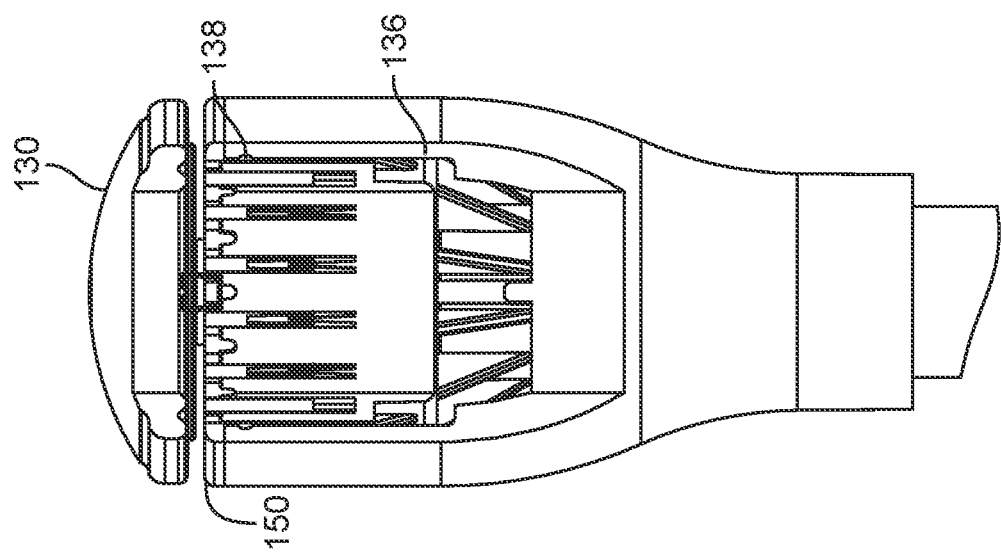
Figure 6C:
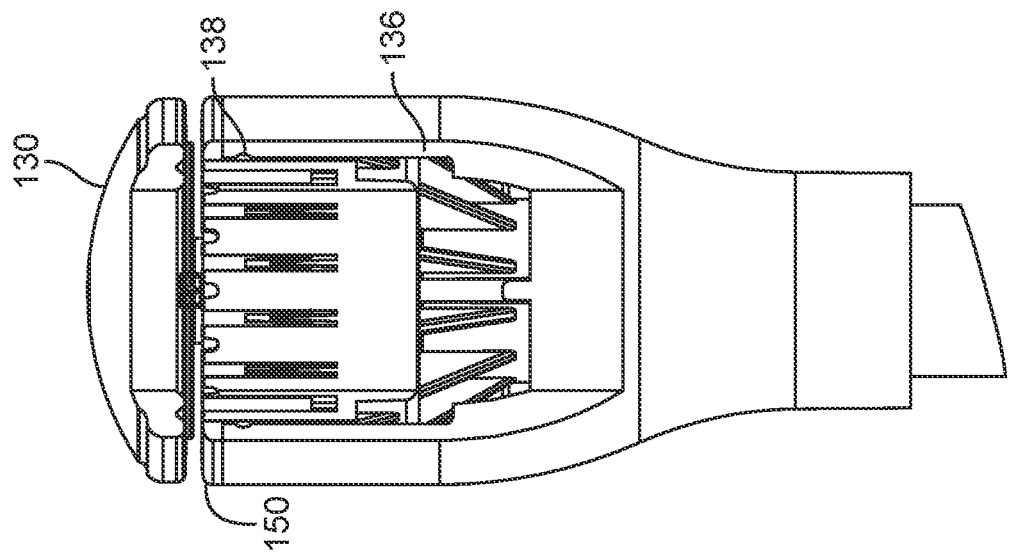

FIG. 6A through FIG. 6C illustrate views depicting the bending of staple 138 subsequent to the firing of circular surgical stapler 100, in accordance with embodiments of the present subject matter. The bending of the staples 138 via the pair of grooves 130B can be seen in FIG. 6A through FIG. 6C. An advantageous factor of the anvil 130 is that its design is not pocketed, which is the case with the conventional anvils. The anvil 130 has grooves 130B instead of pockets for receiving the staples 138 therewithin. Such a design gives a lot of flexibility to the applicability of the anvil. More specifically, the design of the anvil 130 need not be changed according to the number of staples 138. Furthermore, the concept of configuring grooves 130B on the anvil 130 is not only limited to the circular staplers, but can be implemented on many the other kinds of surgical staplers which are not circular but may have, for example, a straight profile.

Figure 7C:
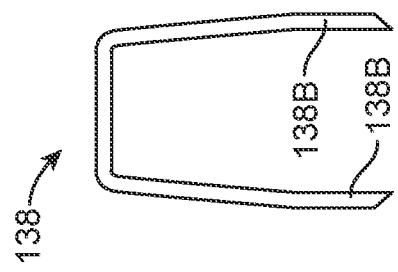
FIG. 7C illustrates a perspective view of a staple, in accordance with an embodiment of the present subject matter.
Figure 7B:
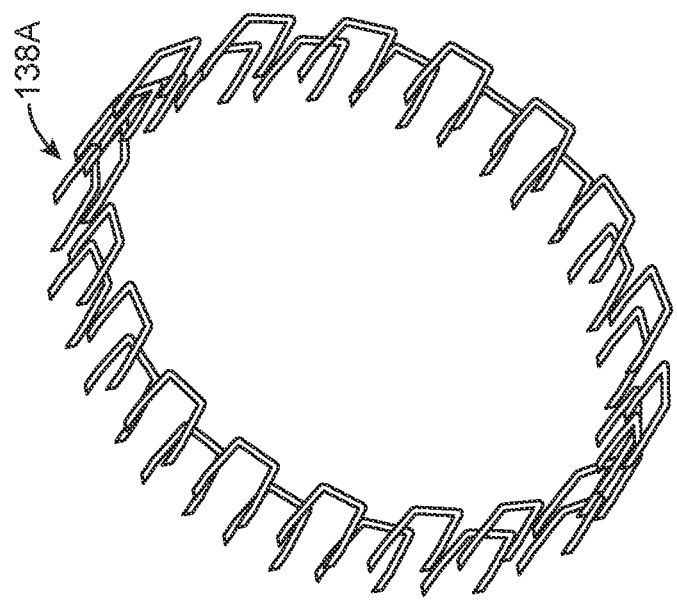
FIG. 7B illustrates a perspective view of a staple cartridge used in the stapler, in accordance with an embodiment of the present subject matter.

FIG. 7A illustrates another perspective view depicting the anvil 130 along with the arrangement of the staples 138 along the periphery of the distal end 102A. FIG. 7B illustrates a perspective view of a staple cartridge 138A used in the stapler 100, in accordance with an embodiment of the present subject matter. FIG. 7C illustrates a perspective view of a staple 138, in accordance with an embodiment of the present subject matter. One aspect of the staple 138 is that legs 138B of the staple 138 have a pre-bent configuration. The pre-bent configuration of the legs 138B allow the legs 138B to deformed in a predictable controlled manner when the stapler 100 is fired. The pre-bend assures the staples 138 will predictably form, without the need for pockets containing ramped angles for the tips to slide on. With proper anvil lubrication, the pre-bent leg 138B is fully sufficient to ensure the staple bends reliably every time. In accordance with one embodiment, the staples are plated, coated, or impregnated with at least one material selected from a group consisting of polytetrafluoroethylene (PTFE), stearate emulsions, and greases, wherein when the at least one material interacting with the malleable metal staple, generates a coefficient of friction less than or equal to 0.5, whether static or sliding.

It is to be noted that one disadvantageous aspect of the conventional circular staplers is the difficulty of firing the device due to the high force to squeeze the firing lever to form the staples and cut the knife backing washer and tissue. To this end, an improved actuation mechanism including the first knob 104, the second knob 106, and the associated components have been described herein. The actuation mechanism uses a combination of improvements including the use of a high mechanical advantage firing system comprising a drive screw, low coefficient of friction components, and pre-bent staples with smaller wire diameters, all combined. More specifically, the use of knobs instead of levers makes it very convenient to fire the staples. Furthermore, the unique pre-bent profile of the staple 138 described herein, in combination with first and second knobs 104, 106, and the use of low coefficient of friction components or adequately lubricated components provides an ease of usage not found in the conventional circular staplers having an actuation lever.

Another advantageous aspect of the stapler 100 is the simple configuration of the stapler. More specifically, the design of the stapler 100, in accordance with the present subject matter, includes very few components as compared to the designs of the conventional circular staplers, which is achieved by replacing the firing lever with a high mechanical advantage rotary firing mechanism and by combining multiple components into fewer components where sensible and were possible to accomplish this without sacrificing function. The reduced number of components also have an added advantage in terms being economical for manufacturing. It is important to note that the present invention is not limited to circular staplers, but can be included in various surgical staplers, e.g. linear or curved staplers, both open and laparoscopic, and whether or not they contain a cutter to subsequently transect tissue following the stapling. The reduced number of components also has an added advantage of ensuring that the surgical stapler 100 has a simple operation. Furthermore, the presence of a single rotary actuator for stapling, tissue cutting, as well as retraction of the trocar makes the stapler 100 intuitive and easy to use, while reducing the time required by the practitioner to familiarize himself with the stapler 100.

Yet another advantageous aspect of the stapler 100, in accordance with an embodiment of the present subject matter, is its sequential operation. Sequential operation refers to the feature of the stapler 100 in which the knife of the stapler is actuated only after the staples have been fired to join the required tissues. This means that knife of the stapler 100 is actuated only after the tissues that are required to be joined are stapled together. Such a feature eliminates the possibility of accidentally cutting the tissues that are required to be joined before they are stapled together.

Another advantageous aspect of the stapler 100, in accordance with the present subject matter, is that incomplete firing of the staples is eliminated due to the sequential firing of the staples as well as the simple and easy to use design of the stapler 100. Therefore, the conditions occurring from such incomplete firing such as poor hemostasis, leaky anastomosis, patient harm or death, are substantially prevented using the stapler 100, in accordance with an embodiment of the present subject matter.

A typical problem with the conventional staplers is that the clinicians don't open the device consistently to the same level prior to removal, which may result in the disruption of the anastomosis upon device removal and may cause immense harm or even death to the patient. The stapler 100, in accordance with an embodiment of the present subject matter, includes a specifically designed release mechanism that includes the auto-open button 126 and other components associated thereto to ensure fast, easy, and uniform opening of the stapler 100 prior to the removal of the stapler 100 from the patient's body.

Figure 8A:
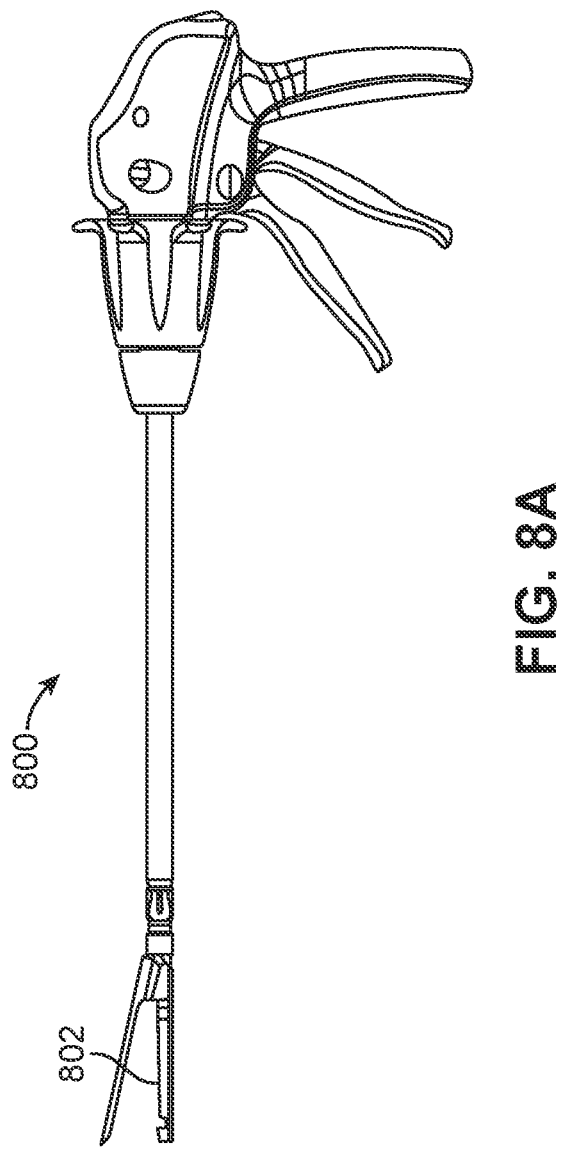
FIG. 8A illustrates a perspective view of a conventional linear surgical stapler having a linear anvil installed thereon, in accordance with an embodiment of the present subject matter.
Figure 8B:
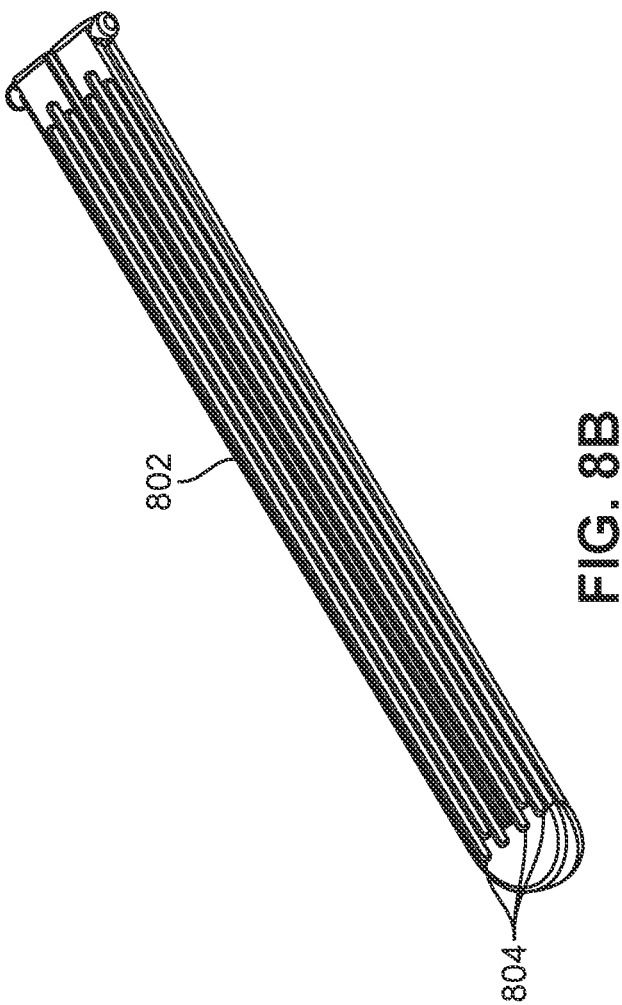
FIG. 8B and FIG. 8C illustrate different views of the linear anvil, in accordance with an embodiment of the present subject matter.
Figure 8C:
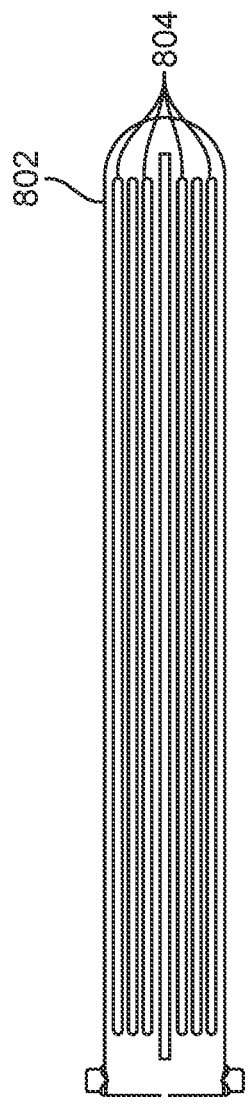

FIG. 8A illustrates a perspective view of a conventional linear surgical stapler Boo having a linear anvil 802 installed thereon, in accordance with an embodiment of the present subject matter. FIG. 8B and FIG. 8C illustrate different views of the linear anvil 802, in accordance with an embodiment of the present subject matter. Referring to FIG. 8A through FIG. 8C, the linear anvil 802 may be configured on usage of any kind of linear surgical stapler, and the linear surgical stapler Boo is only one example of the surgical stapler on which the linear anvil 802 may be installed. The linear anvil 802 includes a plurality of staple grooves 804 configured thereon. The plurality of staple grooves 804 may be arranged in the form of two different sets of grooves that may be configured adjacent to one another depending upon the surgical requirements.

Figure 9A:
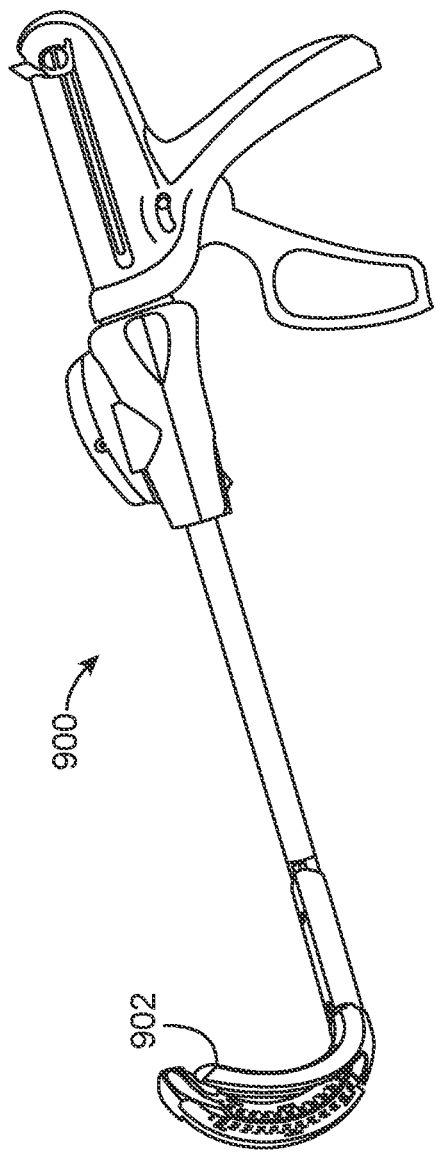
FIG. 9A illustrates a perspective view of a conventional curved surgical stapler having a curved anvil installed thereon, in accordance with an embodiment of the present subject matter.
Figure 9C:
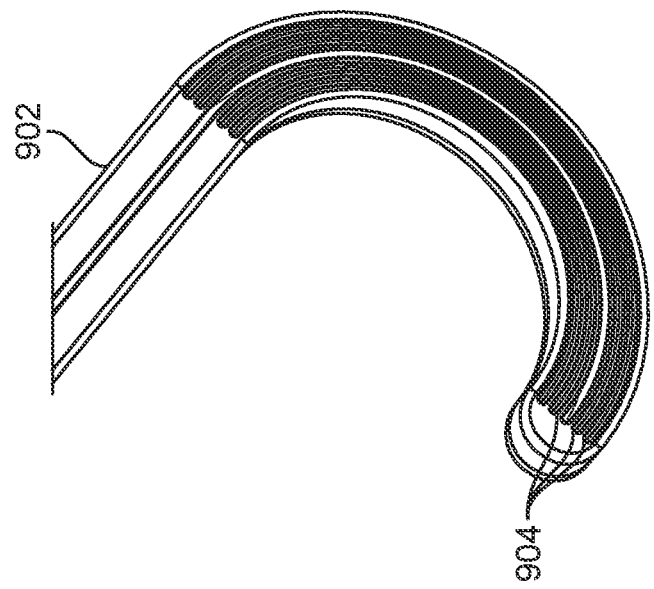
FIG. 9B and FIG. 9C illustrate different views of the curved anvil, in accordance with an embodiment of the present subject matter.
Figure 9B:
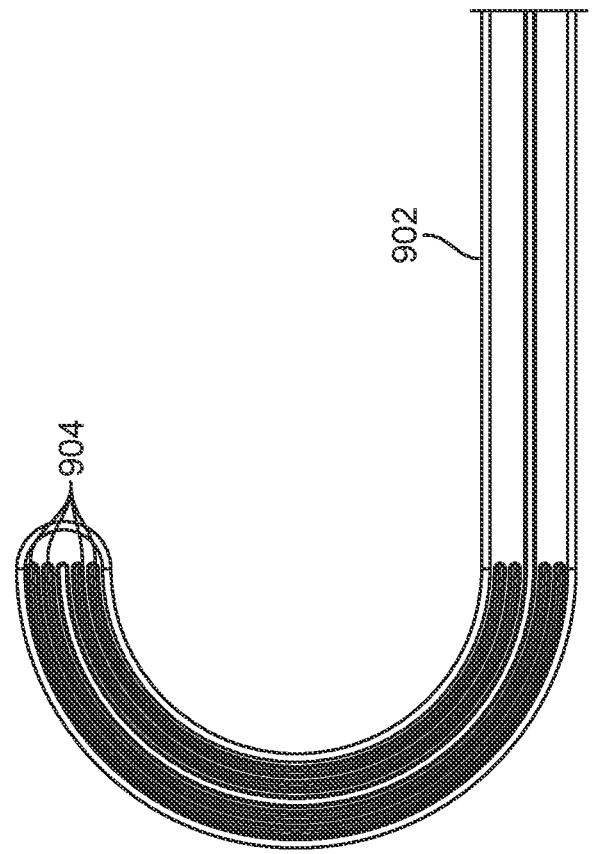

FIG. 9A illustrates a perspective view of a conventional curved surgical stapler 900 having a curved anvil 902 installed thereon, in accordance with an embodiment of the present subject matter. FIG. 9B and FIG. 9C illustrate different views of the curved anvil 902, in accordance with an embodiment of the present subject matter. Referring to FIG. 9A through FIG. 9C, the curved anvil 902 may be configured on usage of any kind of curved surgical stapler, and the curved surgical stapler 900 is only one example of the surgical stapler on which the curved anvil 902 may be installed. The curved anvil 902 includes a plurality of staple grooves 904 configured thereon. The plurality of staple grooves 904 may be arranged in the form of two different sets of grooves that may be configured adjacent to one another depending upon the surgical requirements. It is to be noted that the number of unformed (U-shaped) staples that can be stapled using the anvil of any of the aforementioned shapes per linear centimeter of groove length, in accordance with an embodiment of the present subject matter, is two or more.

A staple guide 150 (seen in FIG. 4H, FIG. 6A through FIG. 6C) is a component of the surgical stapler that guides the staples 138 towards the anvil 130. A staple guide 150 may be a plate having apertures configured thereon for allowing passage of staple legs therefrom for abutment with the anvil 130. A typical staple guide 152 is depicted in FIG. 10A. As seen in FIG. 10A, the typical staple guide 152 comprises a plate 154 having apertures 156 configured thereon. Apertures 156 are typically configured in accordance with pockets formed on the anvil of the conventional surgical staplers. A disadvantageous aspect of the conventional staple guide 152 is that the number of apertures configured on the staple guide 152 is directly impacted by the number of pockets that can be formed on the anvil. This severely impacts the staple density achieved and may cause inadequate stapling of the required tissues.

To overcome the aforementioned disadvantageous aspect, the present subject matter envisages a design a staple guide having improved staple density and can accommodate staples of different sizes. It is to be noted that the improved staple density, in accordance with one embodiment of the present subject matter, is an advantageous aspect of the surgical stapler that is achieved due to the presence of grooves instead of pockets on the anvil.

Figure 10B:
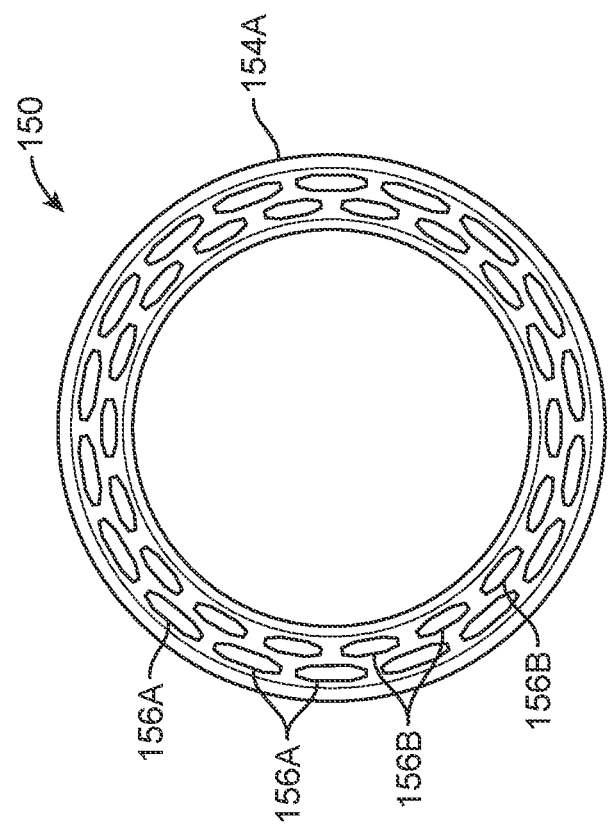
FIG. 10B illustrates a schematic view of a staple guide, in accordance with an embodiment of the present subject matter.
Figure 10A:
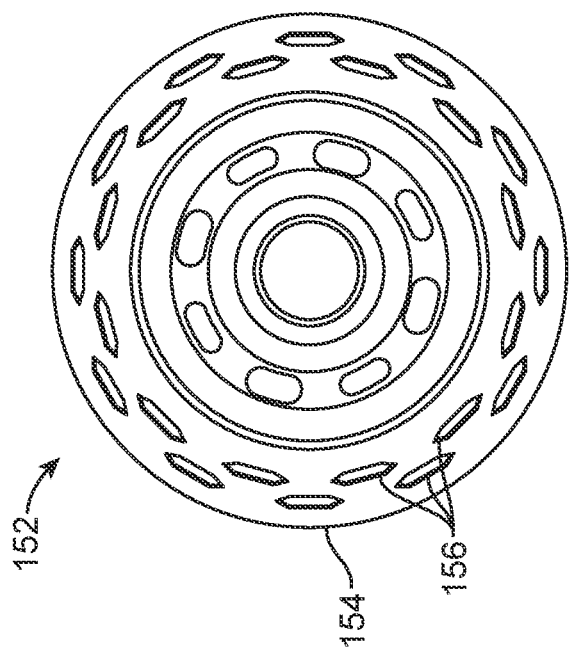
FIG. 10A illustrates a schematic view of a conventional staple guide.

One embodiment of the staple guide 150, in accordance with an embodiment of the present subject matter, is depicted in FIG. 10B. As seen in FIG. 10B, the staple guide 150 comprises a plate 154A having a first array of apertures 156A and a second array of apertures 156B. The first array of apertures 156A, in accordance with one embodiment of the present subject matter, may be configured to allow firing of staple of a first size therefrom. The second array of apertures 156B, in accordance with one embodiment of the present subject matter, may be configured to allow firing of staple of a second size therefrom. In accordance with the instant embodiment, the first array of apertures 156A is an outer ring of bigger sized apertures, while the second array of apertures 156B is an inner ring of smaller sized apertures. An advantageous aspect of the first array of aperture 156A that are bigger sized is that the first array of apertures 156A assist in forming a high B of the staple for blood profusion, whereas the second array of apertures 156B that are smaller sized assist in forming a lower B of the staple for leak prevention and hemostasis at cut line. In one embodiment, the first array of apertures 156A may be configured to run parallel to the second array of apertures 156B, as seen in FIG. 10B. Another embodiment of the staple guide 150 is depicted in FIG. 10C. Referring to FIG. 10C, the second array of apertures 156B may be configured in an inclined manner with respect to the first array of apertures 156A, thereby providing a slight herringbone configuration to the staples on being fired. In one embodiment, the inclination of the second array of apertures may either be in a clockwise direction or an anticlockwise direction.

An anvil 158 for use with the staple guide 152, in accordance with an embodiment of the present subject matter, is depicted in FIG. 11A and FIG. 11B. The anvil 158 comprises an anvil body 160 and a pair of grooves 162A, 162B. The pair of grooves 162A, 162B have a spaced apart configuration, wherein the pair of grooves 162A, 162B have a tissue gripper ridge 164 formed between the pair of grooves 162A, 162B. Referring to FIG. 10B and FIG. 11B, the groove 162A is the outer groove of the anvil 158 configured to coincide and register with the first array of apertures 156A on the staple guide 150. The staples being fired from the first array of apertures 156A are then deformed into the B-shaped final state due to abutment with the groove 162A. Similarly, the groove 162B is configured to deform the staples being fired from the second array of apertures 156B. The tissue gripper ridge 164 has a height that may protrude slightly beyond the face of the anvil for ensuring secure grip of the tissues being stapled by providing a high compression grip area. An outer edge 166 of the anvil 158 has a height lower than that of the tissue gripper ridge 164 and forms the low compression gripping area of the anvil 158.

Another embodiment of the anvil 158A for use with the staple guide 152, in accordance with an embodiment of the present subject matter, is depicted in FIG. 12A and FIG. 12B. The design and configuration of the anvil 158A is identical to that of anvil 158 depicted in FIG. 11A and FIG. 11B, with the only difference being in the profile of the pair of grooves 162A, 162B. As such, the description of the anvil 158A is not repeated herein for the sake of brevity of the present document. Also, like elements of the anvils 158, 158A are denoted using like numerals for the sake of easy readability and simplicity.

Referring to FIG. 12A and FIG. 12B, the pair of grooves 162A, 162B have a B-shaped profile. The B-shaped profile of the pair of grooves 162A, 162B facilitates guided deformation of the staples into a B-shape locking profile of the staple, which may also be seen in FIG. 6A through FIG. 6C.

Figure 13:
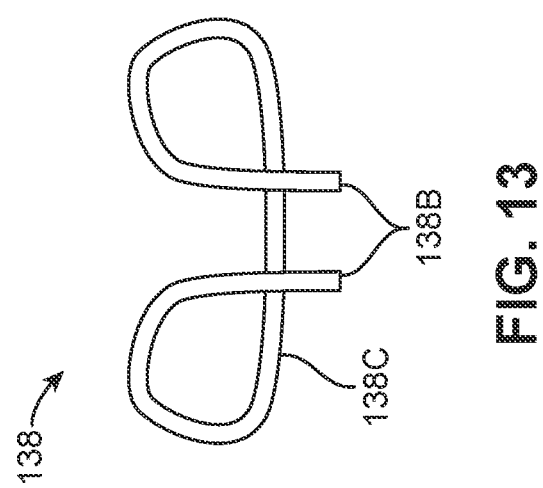
FIG. 13 illustrates a schematic view of a conventional staple wherein legs of the staple exhibit a points past crown phenomenon.

FIG. 13 illustrates a schematic view of a point past crown phenomenon prevalent in some staples 138. In the point past crown phenomenon, the legs 138B of the staple 138 are bent beyond on a crown surface 138C of the staple 138. This phenomenon typically occurs in applications where the staple 138 is required to be bent in a low B profile, i.e., the height of the B shaped profile obtained subsequent to the firing and deformation of the staple is less. Such a phenomenon is undesired since it may cause improper release of the staples subsequent to the firing and may lead to accidental tear of the tissues.

Figure 14A:
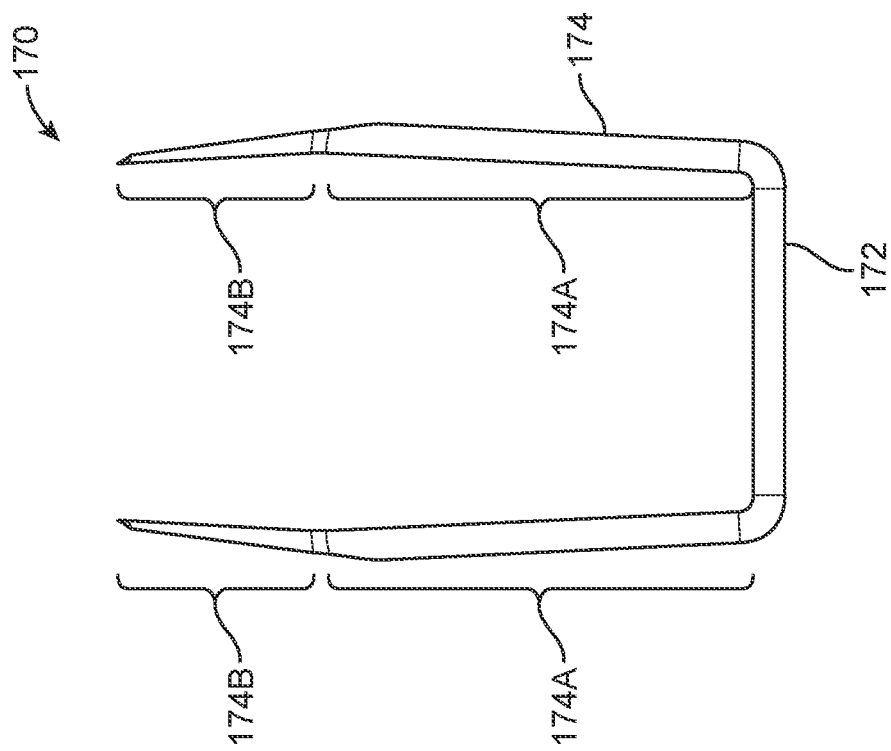
FIG. 14A and FIG. 14B illustrates schematic view of a staple, in accordance with an embodiment of the present subject matter.
Figure 14B:
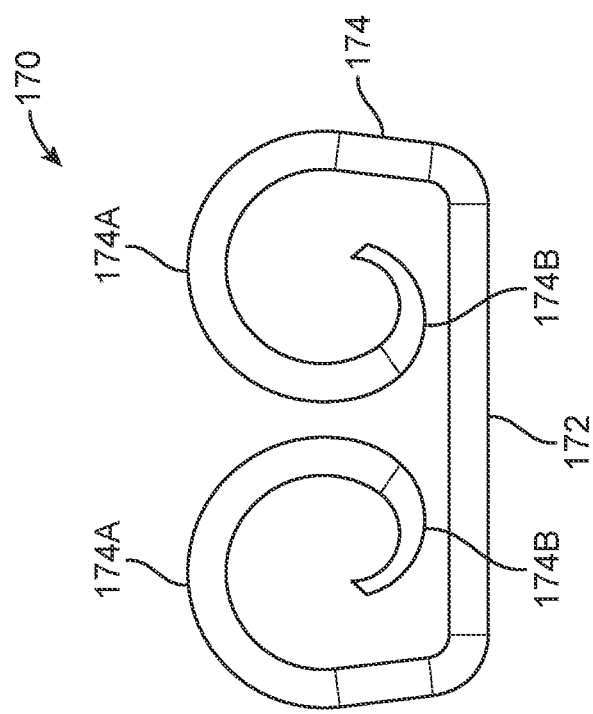

As such, the present subject matter envisages staple 170. The design of the staple 170 is depicted in FIG. 14A. In accordance with an embodiment of the present subject matter, the staple 170 comprises a crown face 172 and a pair of legs 174 extending from the crown face 172. The pair of legs 174 include a first portion 174A and a second portion 174B. In accordance with an embodiment of the present subject matter, the second portion 174B has a chiseled configuration for ensuring smooth B-shaped deformation subsequent to the firing of the staple. In accordance with an embodiment of the present subject matter, the chiseled second portion 174B of the staple 170 may be a soft annealed portion for facilitating easy bending of thereof, while the first portion 174A be a zone that is relatively harder than the second portion yet configured for easy bending. FIG. 14B illustrates a schematic view of the B-shaped profile of the staple 170 subsequent to the firing. The chiseled configuration of the second portion 174B of the staple 170 ensures smooth deformation of staple 170 into a B-shaped locking profile, thereby facilitating mitigation of the point past crown phenomenon. Since the point past crown phenomenon is mitigated, the chances of the staple legs piercing into the tissue after the point past crown phenomenon is mitigated as well, and the staple legs 174 (the bent second portion 174B) press against the tissues instead of getting pierced into due to the legs extending beyond the crown face during the point past crown phenomenon.

Figure 15A:
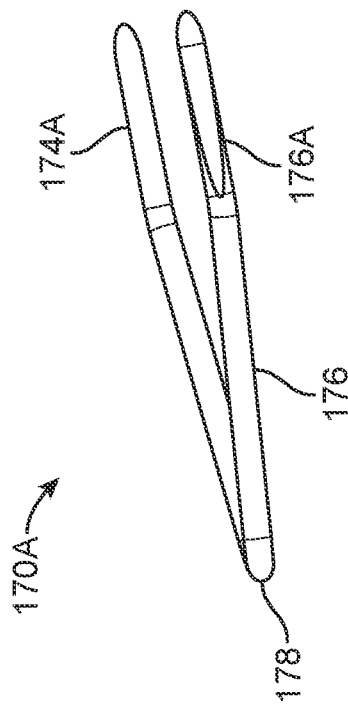
FIG. 15A through FIG. 15C illustrate schematic views of a staple, in accordance with an alternative embodiment of the present subject matter.
Figure 15C:
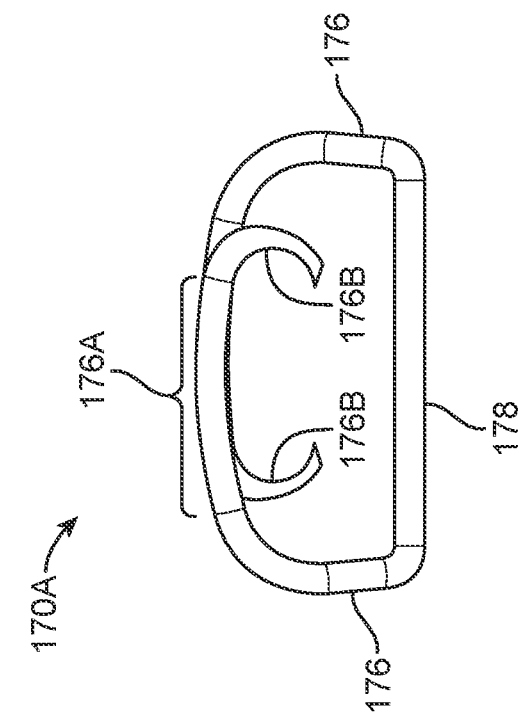
Figure 15B:
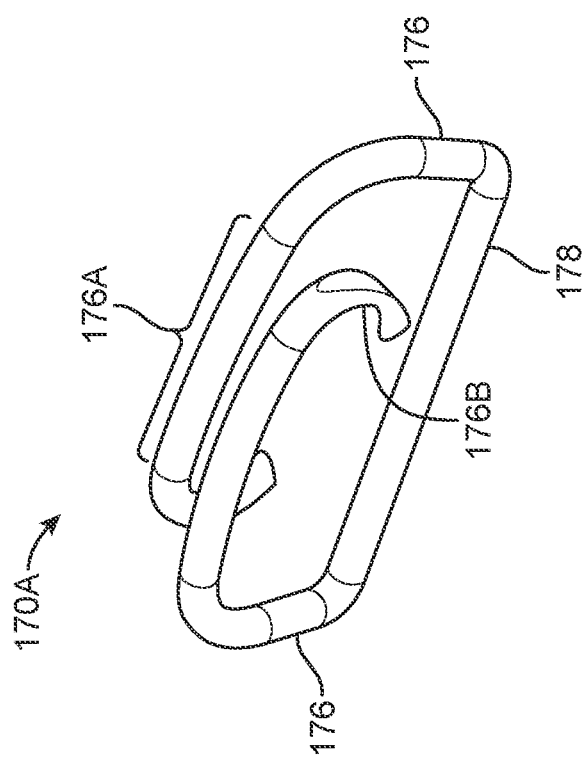

Another embodiment of a staple 170A is depicted in FIG. 15A through FIG. 15C, in accordance with the present subject matter. The staple 170A, in accordance with one embodiment of the present subject matter, includes a pair of out of plane legs 176. It is to be noted that the out of plane legs 176 include a first portion 176A and a second portion 176B. Similar to staple 170, the second portion 176B of the out of plane legs 176B are chiseled portions configured for easy deformation. Such an out of plane configuration of the legs 176 provides a facilitates bending of the legs 176 such that the first portion 176A is bent substantially orthogonally, while the second portion 176B extends substantially orthogonally from the first portion 176A with a curved profile. An advantageous aspect of such a configuration is that it mitigates the point past crown phenomenon.

Figure 16A:
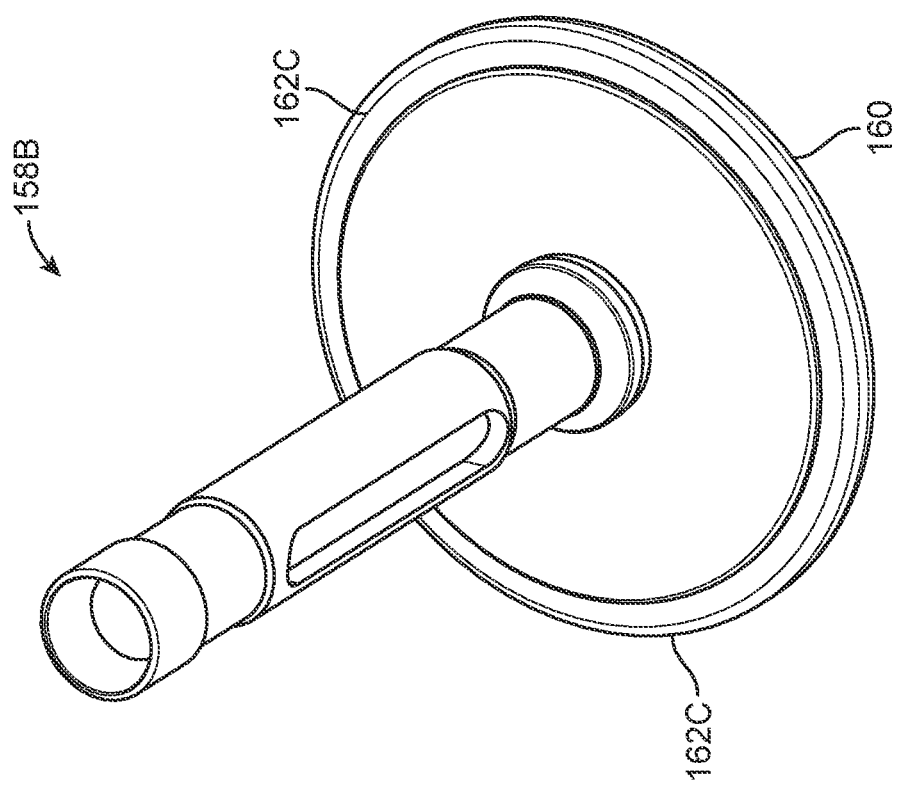

FIG. 16A and FIG. 16B illustrate another embodiment of an anvil 158B having a grooveless configuration. The construction of the anvil 158B is similar to that of anvil 158, 158A with the only difference being that the grooves of anvil 158, 158A are replaced by a depression 162C. The depression 162C extends inwardly from an outer periphery of the anvil body 160 while having a first width. The depression 162C provides a flexibility to the surgical stapler to employ the usage of more than two different arrays of staples without having to configure the corresponding number of grooves.

It is to be noted that configuration of the anvil having plurality of staple forming grooves is a novel feature of the anvil that simplifies the process of design as well as manufacturing the anvil, regardless of the shape of the anvil. The anvil may be circular, linear, or curved or arcuate. More specifically, the provision of the staple forming grooves eliminates the need of anvil having staple forming pockets. An advantageous aspect of the staple forming grooves over staple forming pockets is that the staple forming grooves even if the staples do get misaligned with respect to the staple forming grooves due to some reason, the staples will still deform as required subsequent to the firing. More specifically, in conventional surgical staplers, misalignment of the staple forming pockets with respect to the incoming staples may have disastrous implications, which are completely eliminated by the configuration of the staple forming grooves in the anvil, in accordance with the embodiments of the present subject matter.

In various embodiments, the anvil and trocar may be fabricated from, for example, 300 & 400 Series, 17-4 & 17-7 stainless steel, aluminum, nickel, titanium, and alloys thereof.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK (DuPont de Nemours, Inc., Wilmington, Del.) bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

The foregoing description of the specific embodiments have been described herein above that a person having ordinary skill in the art can apply the current knowledge, readily modify, or adapt for various applications such specific embodiments without departing from the generic concept. All such adaptations and modifications are intended to be comprehended within the meaning and range of equivalents of the disclosed embodiments.

Further, it is to be understood that the terminology employed herein is for the purpose of description and not of limitation. Therefore, while the embodiments herein have been described in terms of preferred embodiments, a person having ordinary skill in the art will readily recognize that the embodiments herein can be practiced with modification within the spirit and scope of the embodiments as described herein.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure is not limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed:

1. A surgical apparatus, comprising:
   (a) a body assembly, comprising:
      (i) a handle portion, and
      (ii) a shaft portion extending distally from the handle portion;
   (b) an end effector comprising a staple driver, wherein the staple driver is movable relative to the shaft portion of the body assembly between an unfired position and a fired position;
   (c) a staple firing actuator located on the handle portion of the body assembly;
   (d) a tissue cutting actuator located on the handle portion of the body assembly;
   (e) a staple containment housing that holds a plurality of unformed metal staples until the moment of dispensing the staples for forming in tissue, wherein each staple from the plurality of unformed metal staples comprises a crown, a crown face, and a pair of legs extending from the crown face, the pair of legs include a first portion and a second portion, wherein the second portion is a soft annealed zone having a chiseled configuration, and a staple guide secured on a free end of the staple containment housing, and wherein the apparatus produces a plurality of formed staples have legs having an out-of-plane configuration, with the leg tips symmetrically biased to arrive on opposite sides of the crown, and
   (f) an anvil assembly for receiving staple tips containing at least one contiguous uninterrupted staple-forming groove of at least the length of two unformed staple widths and which is substantially the same groove depth over its entire length, the at least one contiguous uninterrupted staple-forming groove configured for forming a plurality of staples during the same firing, and wherein the anvil assembly contains at least two contiguous uninterrupted staple-forming depression grooves, and whereby the grooves have varying depths to produce formed staples of varying heights.

2. The surgical apparatus of claim 1, wherein the anvil assembly comprises a circular-shaped distal end effector having at least one fully circular or arcuate groove, and wherein the at least one fully circular or arcuate groove is configured to form a plurality of staples during a single actuation, wherein the number of unformed (U-shaped) staples per linear centimeter of groove length is two or more.

3. The surgical apparatus of claim 1, wherein the anvil assembly comprises a linear distal end effector having at least one straight anvil groove, the at least one straight anvil groove oriented in a fixed or movable (articulable) mode, generally parallel with or up to an angle of 90 degrees to a shaft axis, and wherein the at least one straight anvil groove is configured to form a plurality of staples during a single actuation, wherein the number of unformed (U-shaped) staples per linear centimeter of groove length is two or more.

4. The surgical apparatus of claim 1, wherein the anvil assembly comprises an arcuate distal end effector having at least one circular or arcuate groove configured to form a plurality of staples during a single actuation, wherein the number of unformed (U-shaped) staples per linear centimeter of groove length is two or more.

5. The surgical apparatus of claim 1, wherein the assembly further comprises:
   (g) a tissue release mechanism located within the handle portion of the body assembly, comprising;
      (i) a spring to store mechanical energy during closure of the anvil assembly; and
      (ii) a rotary knob operatively coupled to an elongated shaft and the anvil assembly; and
      (iii) a releasable shaft-engaging mechanism which operatively couples the rotary knob to the anvil during closure and the storage of mechanical energy; and
      (iv) a triggering mechanism to unleash the energy stored in the spring to allow a movable anvil of the anvil assembly to automatically move distally after completing the firing, enabling stapled tissue to easily be released.

6. The surgical apparatus of claim 5, further comprising:
   a tissue compression limiter that is operatively connected to the movable anvil, and comprising at least one tension-limiting spring; and
   a high mechanical advantage staple firing mechanism comprising;
      (i) a slidable elongated driver shaft operatively connected to a staple driver, and containing a screw thread;
      (ii) an adjusting knob operatively connected to the slidable elongated driver shaft, and including a mating screw thread for engagement with the slidable elongated driver shaft.

7. The surgical apparatus according to claim 1, wherein the at least one contiguous uninterrupted staple-forming depression is a groove.

8. The surgical apparatus according to claim 7, wherein the groove has at least one of a U-shaped profile and a B-shaped profile as the forming surfaces of the groove.

9. The surgical apparatus according to claim 7, further comprising a tissue gripping ridge formed operatively adjacent to a pair of contiguous uninterrupted staple-forming depressions, wherein the pair of contiguous uninterrupted staple-forming depressions are grooves configured on the anvil assembly.

10. The surgical apparatus according to claim 1, wherein the at least one contiguous uninterrupted staple-forming depression extends inwardly from an outer periphery of the anvil assembly, the at least one contiguous uninterrupted staple-forming depression having a first width.

11. The surgical apparatus according to claim 1, the staple guide comprises a first array of apertures and a second array of apertures spaced apart from the first array of apertures.

12. The surgical apparatus according to claim 11, wherein the first array of apertures is configured to allow firing of staple of a first size therefrom, and the second array of apertures is configured to allow firing of staple of a second size therefrom.

13. The surgical apparatus according to claim 11, wherein the first array of apertures is configured parallel with respect to the second array of apertures.

14. The surgical apparatus according to claim 11, wherein the second array of apertures is configured in an inclined manner with respect to the first array of apertures.

15. The surgical apparatus according to claim 1, wherein the first portion is relatively harder than the second portion.

16. The surgical apparatus according to claim 15, wherein the staples are plated, coated, or impregnated with at least one material selected from a group consisting of polytetrafluoroethylene (PTFE), wherein when the at least one material interacting with the malleable metal staple, generates a coefficient of friction less than or equal to 0.5, whether static or sliding.

17. The surgical apparatus according to claim 1, wherein the unformed staples include a pre-bent leg, to bias a buckling direction of the staple tips consistently toward each other during device actuation and staple forming, and to reduce column strength of the staple legs to reduce the force required to form the staples.

* * * * *

UNITED STATES PATENT AND TRADEMARK OFFICE
CERTIFICATE OF CORRECTION

PATENT NO. : 11,871,926 B2  
APPLICATION NO. : 17/521048  
DATED : January 16, 2024  
INVENTOR(S) : William Fox Page 1 of 1

It is certified that error appears in the above-identified patent and that said Letters Patent is hereby corrected as shown below:

On the Title Page

In Column 1, Item (73): "Jenei LLC" should be deleted.

Signed and Sealed this  
Thirty-first Day of December, 2024

Derrick Brent  
*Acting Director of the United States Patent and Trademark Office*